*(12)* United States Patent
Lee et al.

(10) Patent No.: US 9,783,808 B2
(45) Date of Patent: Oct. 10, 2017

(54) OVARIAN CANCER-SPECIFIC APTAMERS AND APPLICATIONS THEREOF

(71) Applicant: National Tsing Hua University, Hsinchu (TW)

(72) Inventors: Gwo-Bin Lee, Hsinchu (TW); Lien-Yu Hung, Hsinchu (TW); Chih-Hung Wang, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 303 days.

(21) Appl. No.: 14/558,659

(22) Filed: Dec. 2, 2014

(65) Prior Publication Data

US 2016/0061840 A1    Mar. 3, 2016

(30) Foreign Application Priority Data

Aug. 29, 2014 (TW) .............................. 103129979 A

(51) Int. Cl.
*C12N 15/115* (2010.01)

(52) U.S. Cl.
CPC ........ *C12N 15/115* (2013.01); *C12N 2310/16* (2013.01)

(58) Field of Classification Search
CPC .................................................... C12N 15/115
See application file for complete search history.

(56) References Cited

PUBLICATIONS

Lien-Yu Hung et al., An on-chip Cell-SELEX process for automatic selection of high-affinity aptamers specific to different histologically-classified ovarian cancer cells, Journal Name, 2013, pp. 1-12.

*Primary Examiner* — Jon E Angell
(74) *Attorney, Agent, or Firm* — WPAT, P.C., Intellectual Property Attorneys; Anthony King

(57) ABSTRACT

The present invention provides ovarian cancer-specific aptamers, which are selected in vitro using SELEX and a microfluidic chip system. The aptamers can also bind to different histologically-classified ovarian cancer cells with high affinity accordingly. Therefore, the aptamers of the present invention and the applications thereof can not only be used in detection of ovarian cancer cells but also be applied in recognition of different histologically-classified ovarian cancer cells.

7 Claims, 24 Drawing Sheets
(17 of 24 Drawing Sheet(s) Filed in Color)

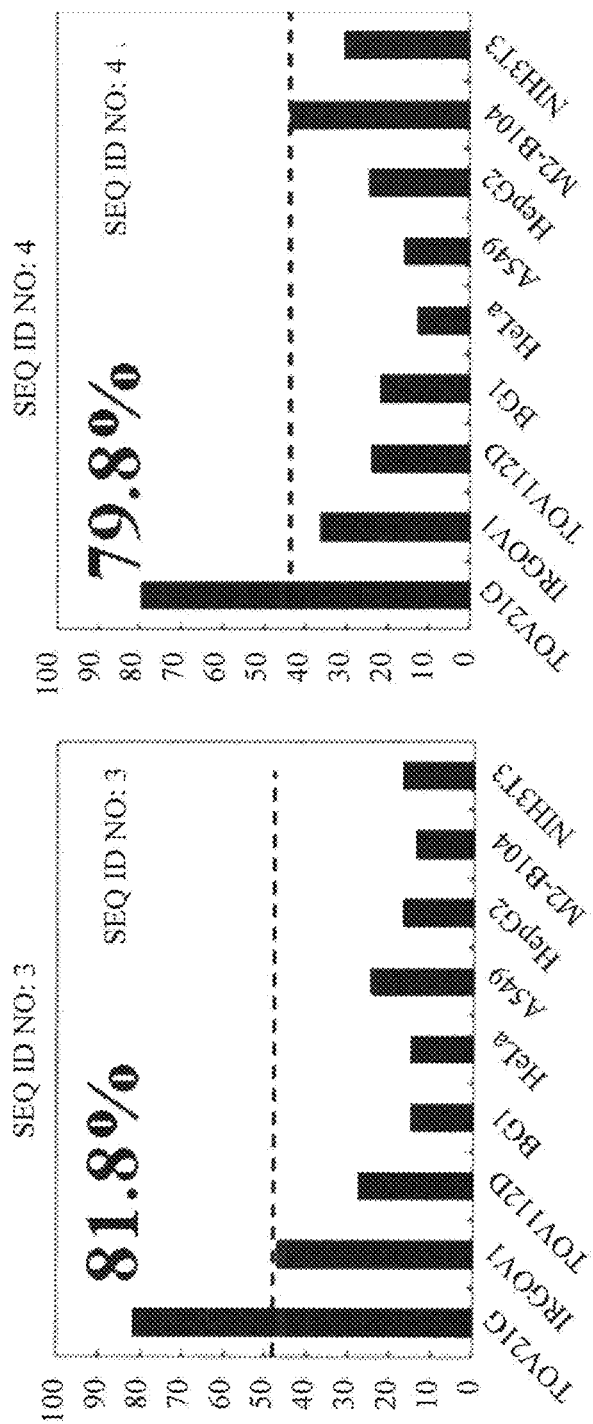
FIG. 4(A) (Continue)

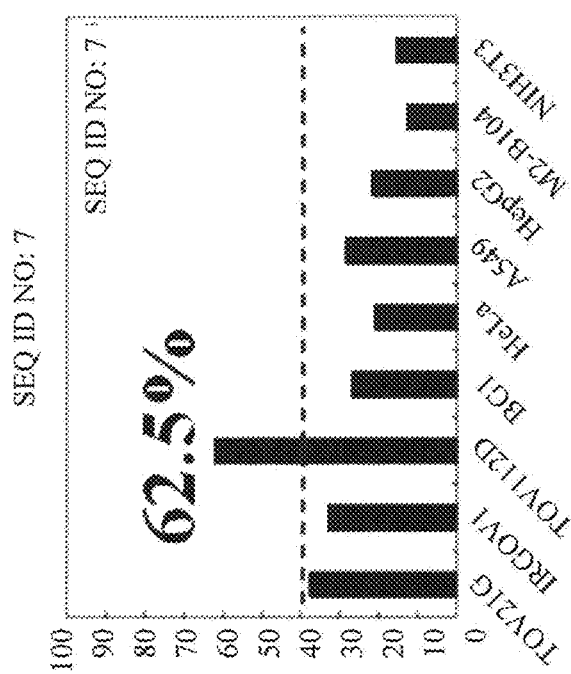
FIG. 4(B) (Continue)

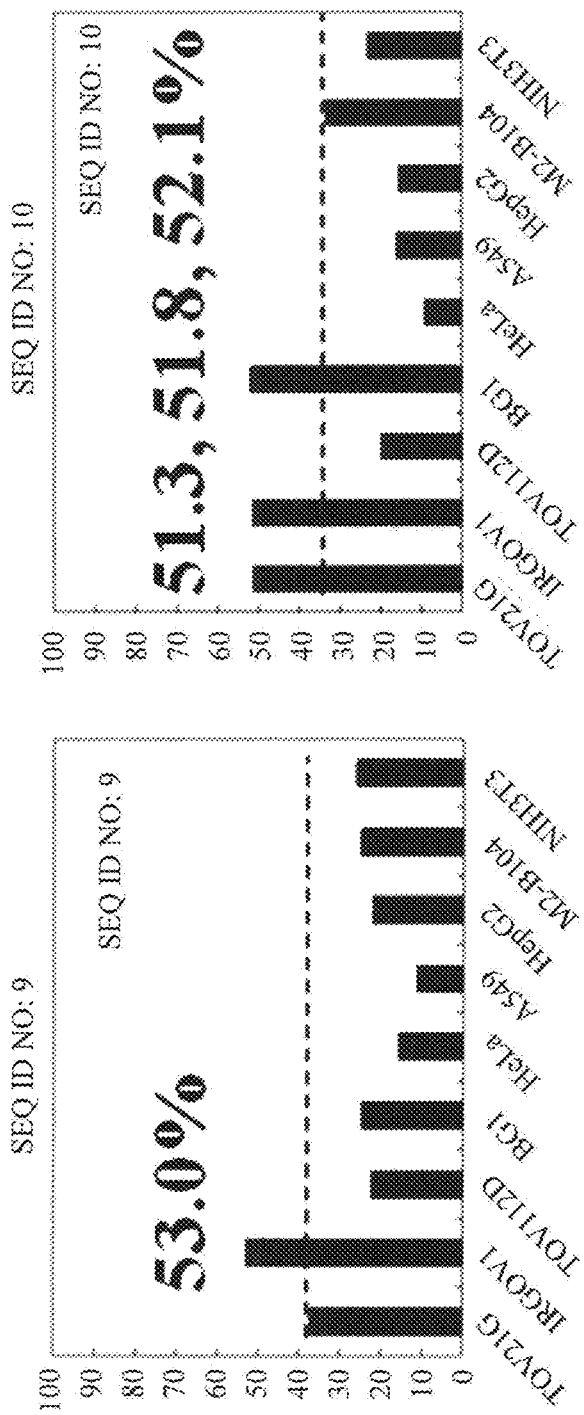
FIG. 4(B) (Continue)

SEQUENCE LISTING

```
<160> NUMBER OF SEQ ID NOS: 28

<210> SEQ ID NO 1
<211> LENGTH: 41
<212> TYPE: DNA
<213> ORGANISM: Artificial Sequence
<220> FEATURE:
<223> OTHER INFORMATION: Sequence specific for clear cell-type ovarian
      cancer cell

<400> SEQUENCE: 1
ccaaaagaag cacgaacaaa aaaaacaagg aaacactact t                          41

<210> SEQ ID NO 2
<211> LENGTH: 41
<212> TYPE: DNA
<213> ORGANISM: Artificial Sequence
<220> FEATURE:
<223> OTHER INFORMATION: Sequence specific for clear cell-type ovarian
      cancer cell

<400> SEQUENCE: 2
aagtagtgtt tccttgtttt ttttgttcgt gcttcttttg g                          41
```

<210> SEQ ID NO 3
<211> LENGTH: 35
<212> TYPE: DNA
<213> ORGANISM: Artificial Sequence
<220> FEATURE:
<223> OTHER INFORMATION: Sequence specific for clear cell-type ovarian
      cancer cell

<400> SEQUENCE: 3
acgtttttgt tcttttgtt gctgttgagt tttgg                          35

<210> SEQ ID NO 4
<211> LENGTH: 36
<212> TYPE: DNA
<213> ORGANISM: Artificial Sequence
<220> FEATURE:
<223> OTHER INFORMATION: Sequence specific for clear cell-type ovarian
      cancer cell

<400> SEQUENCE: 4
ccaaaactca acagcaaaca aaagaacaa aaacgt                          36

<210> SEQ ID NO 5
<211> LENGTH: 34
<212> TYPE: DNA
<213> ORGANISM: Artificial Sequence
<220> FEATURE:
<223> OTHER INFORMATION: Sequence specific for endometrioid-cell type
      ovarian cancer cell

<400> SEQUENCE: 5
cgcactggca ggaagacaaa cacgggacgt tggt                           34

<210> SEQ ID NO 6
<211> LENGTH: 41
<212> TYPE: DNA
<213> ORGANISM: Artificial Sequence
<220> FEATURE:
<223> OTHER INFORMATION: Sequence specific for endometrioid-cell type
      ovarian cancer cell

<400> SEQUENCE: 6
ccaagagcga gagaagaaaa ccgggaaaag gacaactagc t                   41

<210> SEQ ID NO 7
<211> LENGTH: 41
<212> TYPE: DNA
<213> ORGANISM: Artificial Sequence
<220> FEATURE:
<223> OTHER INFORMATION: Sequence specific for endometrioid-cell type
      ovarian cancer cell

<400> SEQUENCE: 7
atcgttggtt ggttttttcg tcttttgttt tctgtgtttg g                   41

<210> SEQ ID NO 8
<211> LENGTH: 41
<212> TYPE: DNA
<213> ORGANISM: Artificial Sequence
<220> FEATURE:
<223> OTHER INFORMATION: Sequence specific for endometrioid-cell type
      ovarian cancer cell

<400> SEQUENCE: 8
ccaaacacag aaaacaaaag acgaaaaaac caaccaacga t                   41

```
<210> SEQ ID NO 9
<211> LENGTH: 41
<212> TYPE: DNA
<213> ORGANISM: Artificial Sequence
<220> FEATURE:
<223> OTHER INFORMATION: Sequence specific for endometrioid-cell type
      ovarian cancer cell

<400> SEQUENCE: 9
ccaaacacaa aaagcgacaa aggcaataga aagataggca t                 41

<210> SEQ ID NO 10
<211> LENGTH: 41
<212> TYPE: DNA
<213> ORGANISM: Artificial Sequence
<220> FEATURE:
<223> OTHER INFORMATION: Sequence specific for endometrioid-cell type
      ovarian cancer cell

<400> SEQUENCE: 10
atgcctatct ttctattgcc tttgtcgctt tttgtgtttg g                 41

<210> SEQ ID NO 11
<211> LENGTH: 36
<212> TYPE: DNA
<213> ORGANISM: Artificial Sequence
<220> FEATURE:
<223> OTHER INFORMATION: Sequence specific for endometrioid-cell type
      ovarian cancer cell

<400> SEQUENCE: 11
ccagcaagac aaacaaaacg aaacaaaaaa aggcat                      36

<210> SEQ ID NO 12
<211> LENGTH: 40
<212> TYPE: DNA
<213> ORGANISM: Artificial Sequence
<220> FEATURE:
<223> OTHER INFORMATION: Sequence specific for serous-cell type ovarian
      cancer cell

<400> SEQUENCE: 12
attggttttt ttttagttgt ttttgctgga tttttccggg                  40

<210> SEQ ID NO 13
<211> LENGTH: 40
<212> TYPE: DNA
<213> ORGANISM: Artificial Sequence
<220> FEATURE:
<223> OTHER INFORMATION: Sequence specific for serous-cell type ovarian
      cancer cell

<400> SEQUENCE: 13
cccggaaaaa tccagcaaaa acaactaaaa aaaaaccaat                  40

<210> SEQ ID NO 14
<211> LENGTH: 72
<212> TYPE: DNA
<213> ORGANISM: Artificial Sequence
<220> FEATURE:
<223> OTHER INFORMATION: Aptamer specific for clear cell-type ovarian
      cancer cell

<400> SEQUENCE: 14
ggcaggatta caaacaccaa agaagcacg aacaaaaaaa acaaggaaac actacttggt   60
ctgtggtgct gt                                                72
```

<210> SEQ ID NO 15
<211> LENGTH: 72
<212> TYPE: DNA
<213> ORGANISM: Artificial Sequence
<220> FEATURE:
<223> OTHER INFORMATION: Aptamer specific for clear cell-type ovarian
      cancer cell

<400> SEQUENCE: 15
acagcaccac agaccaagta gtgtttcctt gttttttttg ttcgtgcttc ttttggtgtt    60
tgtaatcctg cc                                                        72

<210> SEQ ID NO 16
<211> LENGTH: 68
<212> TYPE: DNA
<213> ORGANISM: Artificial Sequence
<220> FEATURE:
<223> OTHER INFORMATION: Aptamer specific for clear cell-type ovarian
      cancer cell

<400> SEQUENCE: 16
tacagcacca cagaccacgt ttttgttctt tttgtttgct gttgagtttt ggtgtttgtc    60
ttcctgcc                                                             68

<210> SEQ ID NO 17
<211> LENGTH: 68
<212> TYPE: DNA
<213> ORGANISM: Artificial Sequence
<220> FEATURE:
<223> OTHER INFORMATION: Aptamer specific for clear cell-type ovarian
      cancer cell

<400> SEQUENCE: 17
ggcaggaaga caaacaccaa aactcaacag caaacaaaaa gaacaaaaac gtggtctgtg    60
gtgctgta                                                             68

<210> SEQ ID NO 18
<211> LENGTH: 65
<212> TYPE: DNA
<213> ORGANISM: Artificial Sequence
<220> FEATURE:
<223> OTHER INFORMATION: Aptamer specific for endometrioid-cell type
      ovarian cancer cell

<400> SEQUENCE: 18
ggcaggaaga caaacacgca ctggcaggaa gacaaacacg ggacgttggt ggtctgtggt    60
gctgt                                                                65

<210> SEQ ID NO 19
<211> LENGTH: 72
<212> TYPE: DNA
<213> ORGANISM: Artificial Sequence
<220> FEATURE:
<223> OTHER INFORMATION: Aptamer specific for endometrioid-cell type
      ovarian cancer cell

<400> SEQUENCE: 19
ggcaggaaga caaacaccaa gagcgagaga agaaaaccgg gaaaaggaca actagctggt    60
ctgtggtgct gt                                                        72

<210> SEQ ID NO 20
<211> LENGTH: 71

```
<212> TYPE: DNA
<213> ORGANISM: Artificial Sequence
<220> FEATURE:
<223> OTHER INFORMATION: Aptamer specific for endometrioid-cell type
      ovarian cancer cell

<400> SEQUENCE: 20
cagcaccaca gaccatcgtt ggttggtttt ttcgtctttt gttttctgtg tttggtgttt      60
gtcttcctgc c                                                          71

<210> SEQ ID NO 21
<211> LENGTH: 71
<212> TYPE: DNA
<213> ORGANISM: Artificial Sequence
<220> FEATURE:
<223> OTHER INFORMATION: Aptamer specific for endometrioid-cell type
      ovarian cancer cell

<400> SEQUENCE: 21
ggcaggaaga caaacaccaa acacagaaaa caaaagacga aaaaaccaac caacgatggt      60
ctgtggtgct g                                                          71

<210> SEQ ID NO 22
<211> LENGTH: 72
<212> TYPE: DNA
<213> ORGANISM: Artificial Sequence
<220> FEATURE:
<223> OTHER INFORMATION: Aptamer specific for endometrioid-cell type
      ovarian cancer cell

<400> SEQUENCE: 22
ggcaggaaga caaacaccaa acacaaaaag cgacaaaggc aatagaaaga taggcatggt      60
ctgtggtgct gt                                                         72

<210> SEQ ID NO 23
<211> LENGTH: 72
<212> TYPE: DNA
<213> ORGANISM: Artificial Sequence
<220> FEATURE:
<223> OTHER INFORMATION: Aptamer specific for endometrioid-cell type
      ovarian cancer cell

<400> SEQUENCE: 23
acagcaccac agaccatgcc tatctttcta ttgcctttgt cgcttttttgt gtttggtgtt    60 tgtcttcctg cc                                                         72

<210> SEQ ID NO 24
<211> LENGTH: 68
<212> TYPE: DNA
<213> ORGANISM: Artificial Sequence
<220> FEATURE:
<223> OTHER INFORMATION: Aptamer specific for endometrioid-cell type
      ovarian cancer cell

<400> SEQUENCE: 24
ggcaggaaga caaacaccag caagacaaac aaaacgaaac aaaaaaaggc atggtctgtg     60
gtgctgta                                                              68

<210> SEQ ID NO 25
<211> LENGTH: 60
<212> TYPE: DNA
<213> ORGANISM: Artificial Sequence
<220> FEATURE:
<223> OTHER INFORMATION: Aptamer specific for serous-cell type ovarian
``` cancer cell

<400> SEQUENCE: 25
tacagcacca cagaccattg gttttttttt agttgttttt gctggatttt tccgggtgtt    60

<210> SEQ ID NO 26
<211> LENGTH: 72
<212> TYPE: DNA
<213> ORGANISM: Artificial Sequence
<220> FEATURE:
<223> OTHER INFORMATION: Aptamer specific for serous-cell type ovarian
      cancer cell

<400> SEQUENCE: 26
ggcaggaaga caaacacccg gaaaaatcca gcaaaaacaa ctaaaaaaaa accaatggtc    60
tgtggtgctg ta    72

<210> SEQ ID NO 27
<211> LENGTH: 16
<212> TYPE: DNA
<213> ORGANISM: Artificial Sequence
<220> FEATURE:
<223> OTHER INFORMATION: Forward primer

<400> SEQUENCE: 27
ggcaggaaga caaaca    16

<210> SEQ ID NO 28
<211> LENGTH: 16
<212> TYPE: DNA
<213> ORGANISM: Artificial Sequence
<220> FEATURE:
<223> OTHER INFORMATION: Reverse primer

<400> SEQUENCE: 28
acagcaccac agacca    16

OVARIAN CANCER-SPECIFIC APTAMERS AND APPLICATIONS THEREOF

CROSS-REFERENCES TO RELATED APPLICATIONS

This application claims priority to Taiwan Patent Application No. 103129979 filed on 29 Aug. 2014. All disclosure of which is incorporated herein by reference in its entirety.

BACKGROUND OF THE INVENTION

1. Field of the Invention

The present invention is related to an ovarian cancer-specific aptamer; more specifically, the present invention is related to aptamers specific for different histologically-classified ovarian cancer cells and the applications thereof.

2. the Prior Arts

Cancer, also known as malignant tumor, is a leading cause of millions of death annually, and is also the top one most lethal disease in Taiwan over the past decade. Among the various cancers, ovarian cancer is one of the most common gynecological cancers, only next to cervical cancer, and takes the second place of the most common cancer in Taiwanese female population. Yet, in comparison to cervical cancer, with early diagnosis and proper treatment, the prognosis and survival rate of ovarian cancer are often relatively high. For instance, patients diagnosed with stage I ovarian cancer have a five-year survival rate of 89%, which drops to only 17% if diagnosed at stage IV. Unfortunately, most ovarian cancers are not easily to be diagnosed in their early stages due to insignificant symptoms, and often not until the tumor grow large enough to suppress the large intestine and result in conditions such as constipation, diarrhea, nausea, and flatulence, can the tumor be discovered. Hence, most ovarian cancers are diagnosed at stage III or later, along with tumor migration, resulting in poor prognosis.

Clinically, ovarian cancer detection methods often include virginal ultrasonic examination and Doppler ultrasound examination, which are able to determine the vascular distribution and blood flow of the tumor; however, due to the fact that ovary with ovarian cancer is similar to a normal one in size and appearance, such ultrasonic examinations still lack reliability. On the other hand, serum tumor markers, such as human chorionic gonadotropin (hCG), carcinoembryonic antigen (CEA), and α-fetoprotein (α-FP), are also used for the detection of ovarian cancer. However, most serum tumor makers having relatively poor detecting ability for early stage tumor comparing to tumor that reoccurred after surgery are not suitable for early stage detection of ovarian cancer.

In light of the fact the there are still no effective detection for early-stage ovarian cancer diagnosis, it is of great necessity to develop substitutes with high specificity to ovarian cancer cells for traditional serum tumor markers for future clinical research as well as rapid detection of ovarian cancer at its early stage, which promotes prognosis and survival rate. Meanwhile, currently, the market still lacks accurate and cost-effective markers or methods for detection and recognition of different histologically-classified ovarian cancer cells.

SUMMARY OF THE INVENTION

As a result, the present invention provides an ovarian cancer-specific aptamer, comprising: (a) a nucleic acid sequence specific for ovarian cancer cell; and (b) a forward primer or a reverse primer; wherein the nucleic acid sequence specific for ovarian cancer cell is selected from: (i) the group consisting of SEQ ID NO: 1, SEQ ID NO: 2, SEQ ID NO: 3, SEQ ID NO: 4, and any combination thereof; (ii) the group consisting of SEQ ID NO: 5, SEQ ID NO: 6, SEQ ID NO: 7, SEQ ID NO: 8, SEQ ID NO: 9, SEQ ID NO: 10, SEQ ID NO: 11, and any combination thereof; or (iii) the group consisting of SEQ ID NO: 12, SEQ ID NO: 13, and the combination thereof.

In one embodiment of the present invention, the ovarian cancer cell is a clear-cell type ovarian cancer cell, an endometrioid-cell type ovarian cancer cell, or a serous-cell type ovarian cancer cell. The forward primer is SEQ ID NO: 27, and the reverse primer is SEQ ID NO: 28. The aptamer of the present invention contains at least one stem-loop secondary structure.

In one embodiment of the present invention, when the ovarian cancer cell is the clear-cell type ovarian cancer cell, the aptamer of SEQ ID NO: 14, SEQ ID NO: 15, SEQ ID NO: 16, SEQ ID NO: 17, SEQ ID NO: 23, or any combination thereof is used.

In another embodiment of the present invention, when the ovarian cancer cell is the endometrioid-cell type ovarian cancer cell, the aptamer of SEQ ID NO: 18, SEQ ID NO: 19, SEQ ID NO: 20, SEQ ID NO: 21, SEQ ID NO: 22, SEQ ID NO: 23, SEQ ID NO: 24, or any combination thereof is used.

In still another embodiment of the present invention, when the ovarian cancer cell is a serous-cell type ovarian cancer cell, the aptamer of SEQ ID NO: 23, SEQ ID NO: 25, SEQ ID NO: 26, or any combination thereof is used.

Another aspect of the present invention is to provide a method for detecting the existence of ovarian cancer cell in a subject, comprising: (a) contacting a sample from the subject with at least one aptamer of the present invention that specifically binds to the ovarian cancer cell; and (b) detecting the existence of the ovarian cancer cell in the sample bounded with the aptamer of step (a), if any; wherein the SEQ ID NO: 14, SEQ ID NO: 15, SEQ ID NO: 16, SEQ ID NO: 17, or SEQ ID NO: 23 is selected if step (b) determines the existence of clear-cell type ovarian cancer cell; the SEQ ID NO: 18, SEQ ID NO: 19, SEQ ID NO: 20, SEQ ID NO: 21, SEQ ID NO: 22, SEQ ID NO: 23, or SEQ ID NO: 24 is selected if step (b) determines the existence of endometrioid-cell type ovarian cancer cell; the SEQ ID NO: 23, SEQ ID NO: 25, or SEQ ID NO: 26 is selected if step (b) determines the existence of serous-cell type ovarian cancer cell. The aptamer of the present is conjugated to a label; said label is a fluorescence label, a luminescence label, a radioactive isotope, an enzymatic label, or a biotin. In one embodiment of the present invention, the method for detecting the existence of ovarian cancer cell in a subject further comprises conjugating the aptamer to a surface of a magnetic bead to form an aptamer-conjugated magnetic bead and the ovarian cancer cell is captured by the aptamer-conjugated magnetic bead and a magnetic field is used to isolate the aptamer-conjugated magnetic bead bound with the ovarian cancer cell.

Another aspect of the present invention is to provide a microfluidic chip comprising the aptamer according to the present invention.

The aptamers of the present invention bind to different histologically-classified ovarian cancer cells with high specificity and high affinity, which can be used for rapid detection of ovarian cancer cells as well as recognition of ovarian cancer cells according to their histological classifications. Furthermore, the aptamers of the present invention are small in terms of molecular weight and are stable in heat, resistant to degradation, and capable of long term storage. The aptamers of the present invention can also be reused and be attached to other molecules easily. Thus, the aptamers of the present invention can readily replace antibodies as serum tumor markers for accurate and cost-effective detection of ovarian cancer.

The present invention is further explained in the following embodiment illustration and examples. Those examples below should not, however, be considered to limit the scope of the invention, and it is contemplated that modifications will readily occur to those skilled in the art, which modifications will be within the spirit of the invention and scope of the appended claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE PREFERRED EMBODIMENT

Figure 1:
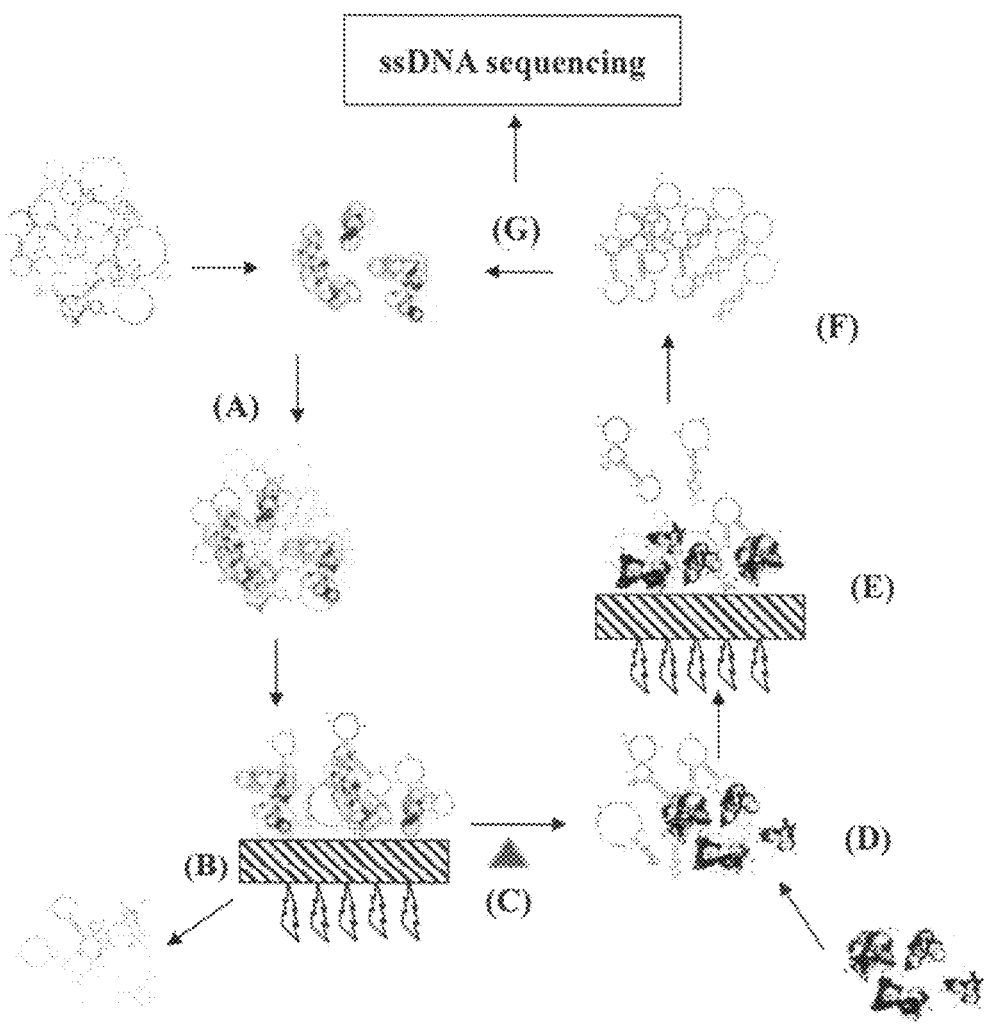
FIG. 1, the flow chart of SELEX selection of aptamers specific for target cells using a microfluidic chip.
Figure 2A:
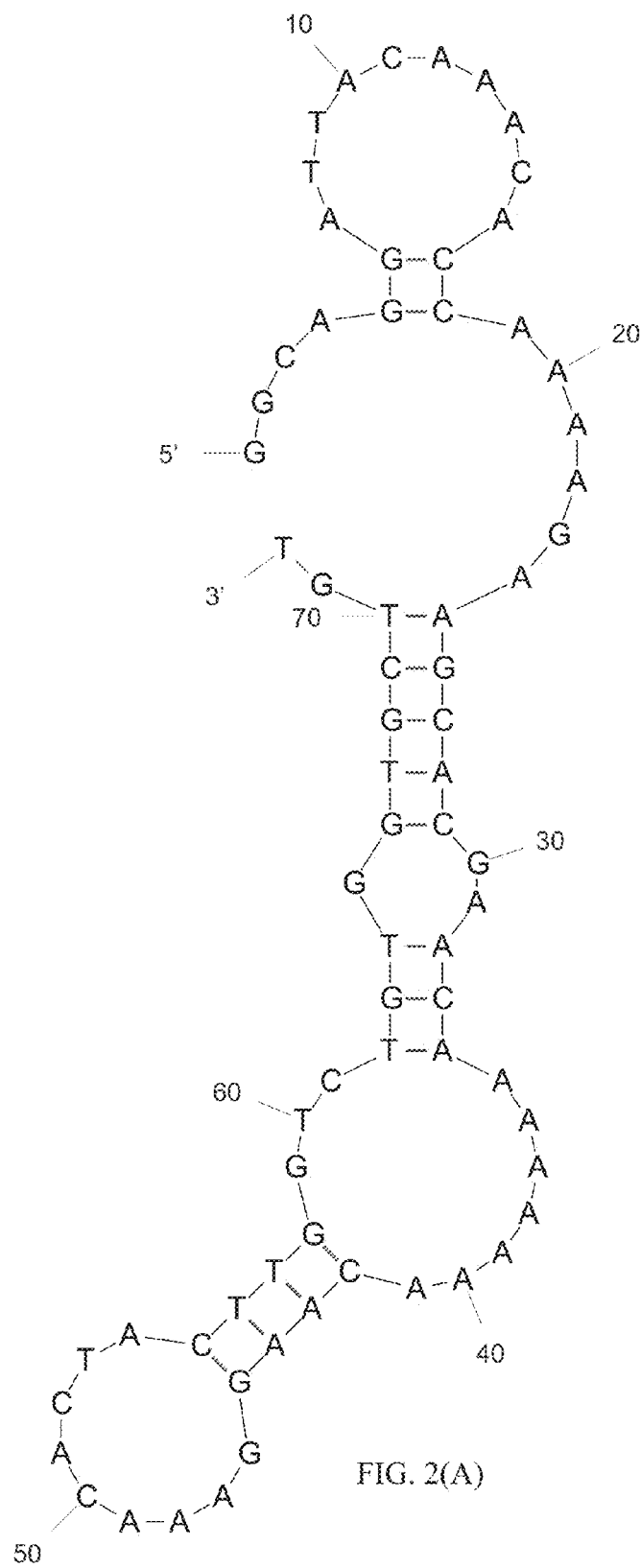
FIG. 2(A)-2(M), secondary structures of the aptamer of the present invention, wherein (A)-(D) and (J) are the aptamers specific for clear-cell type ovarian cancer cell TOV21G (SEQ ID NO: 14-17 and 23); (E)-(K) are the aptamers specific for endometrioid-cell type ovarian cancer cell TOV112D and IGROV1 (SEQ ID NO: 18-24); (J) and (L)-(M) are aptamers specific for serous-cell type ovarian cancer cell BG1 (SEQ ID NO: 23 and 25-26).
Figure 2B:
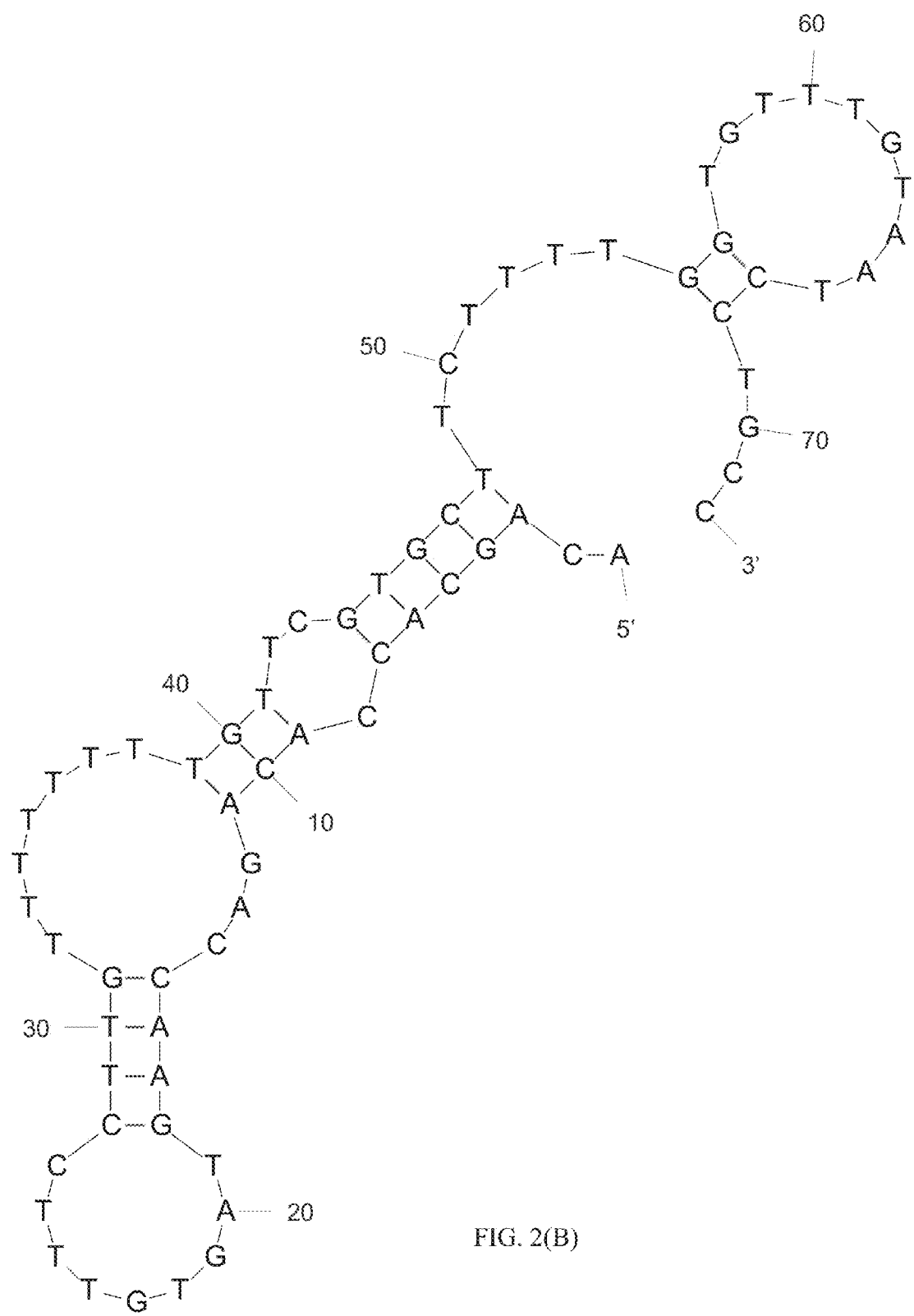
Figure 2C:
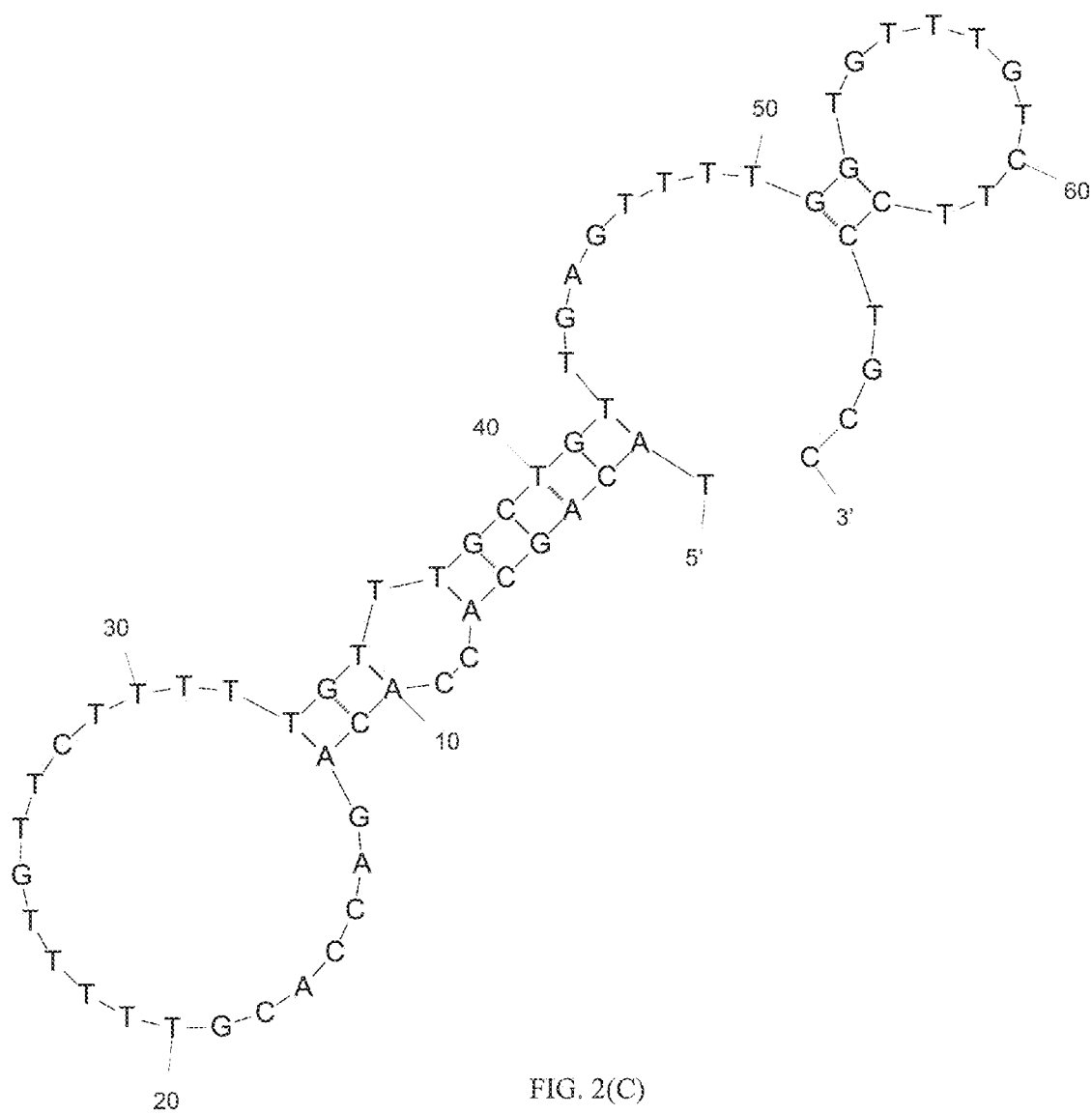
Figure 2D:
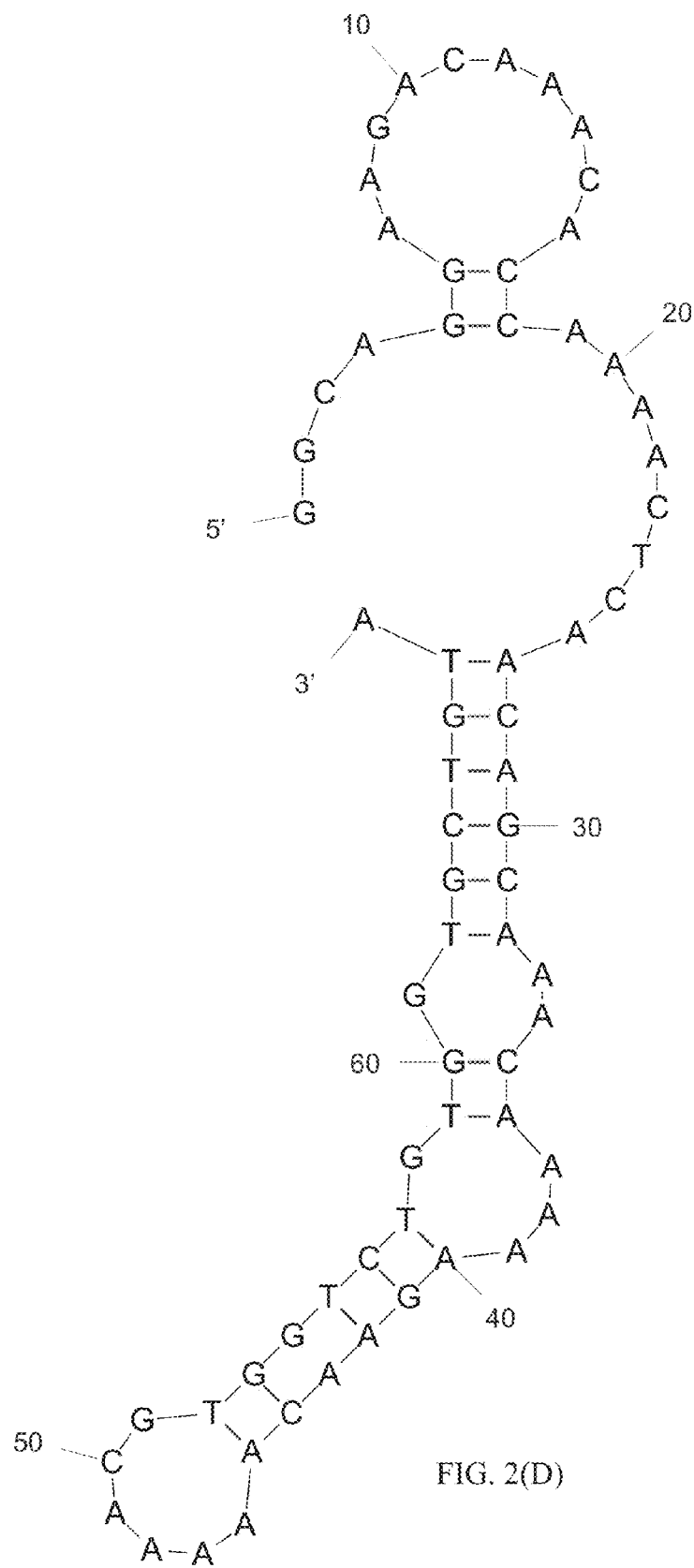
Figure 2E:
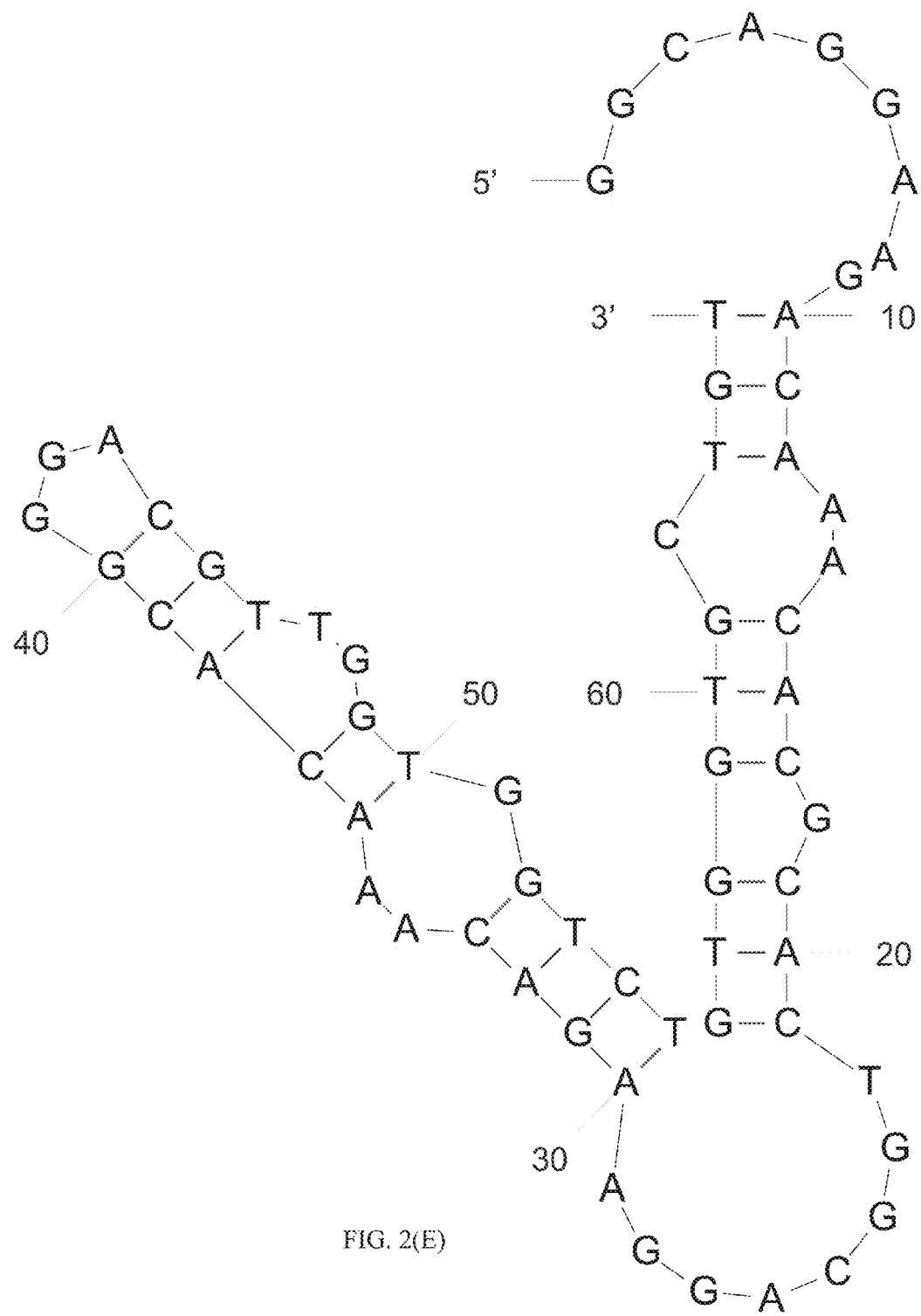
Figure 2F:
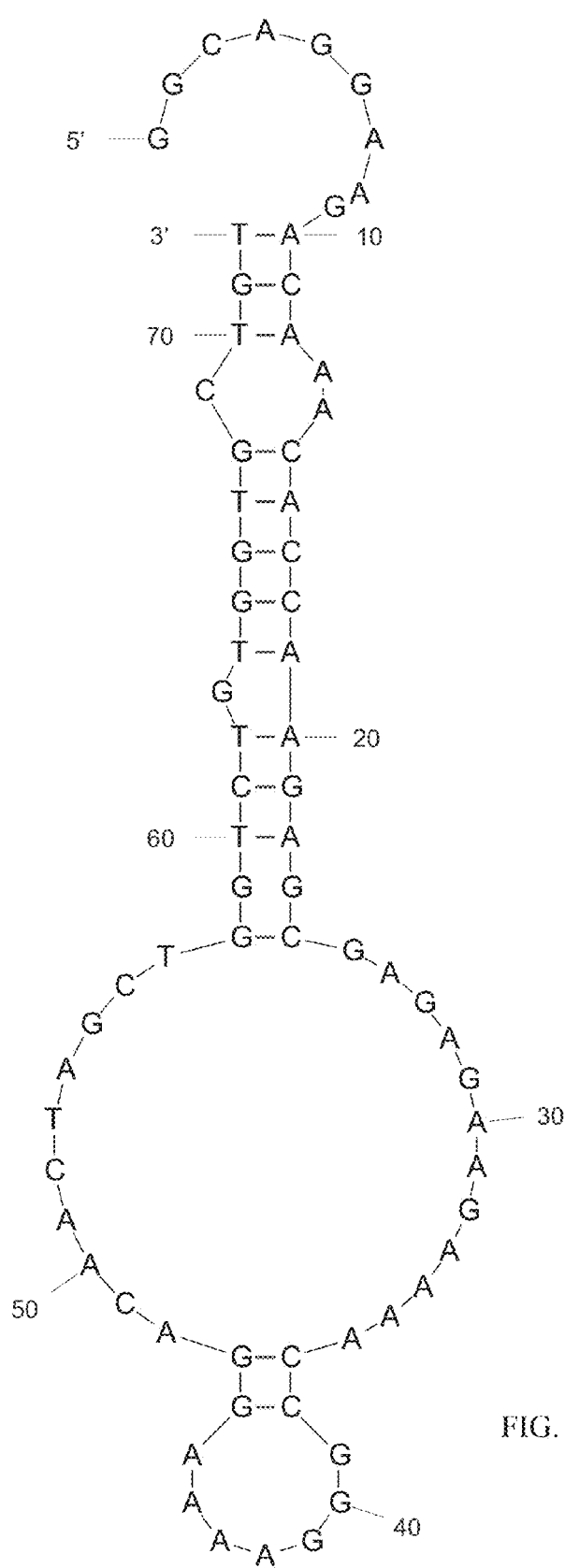
Figure 2G:
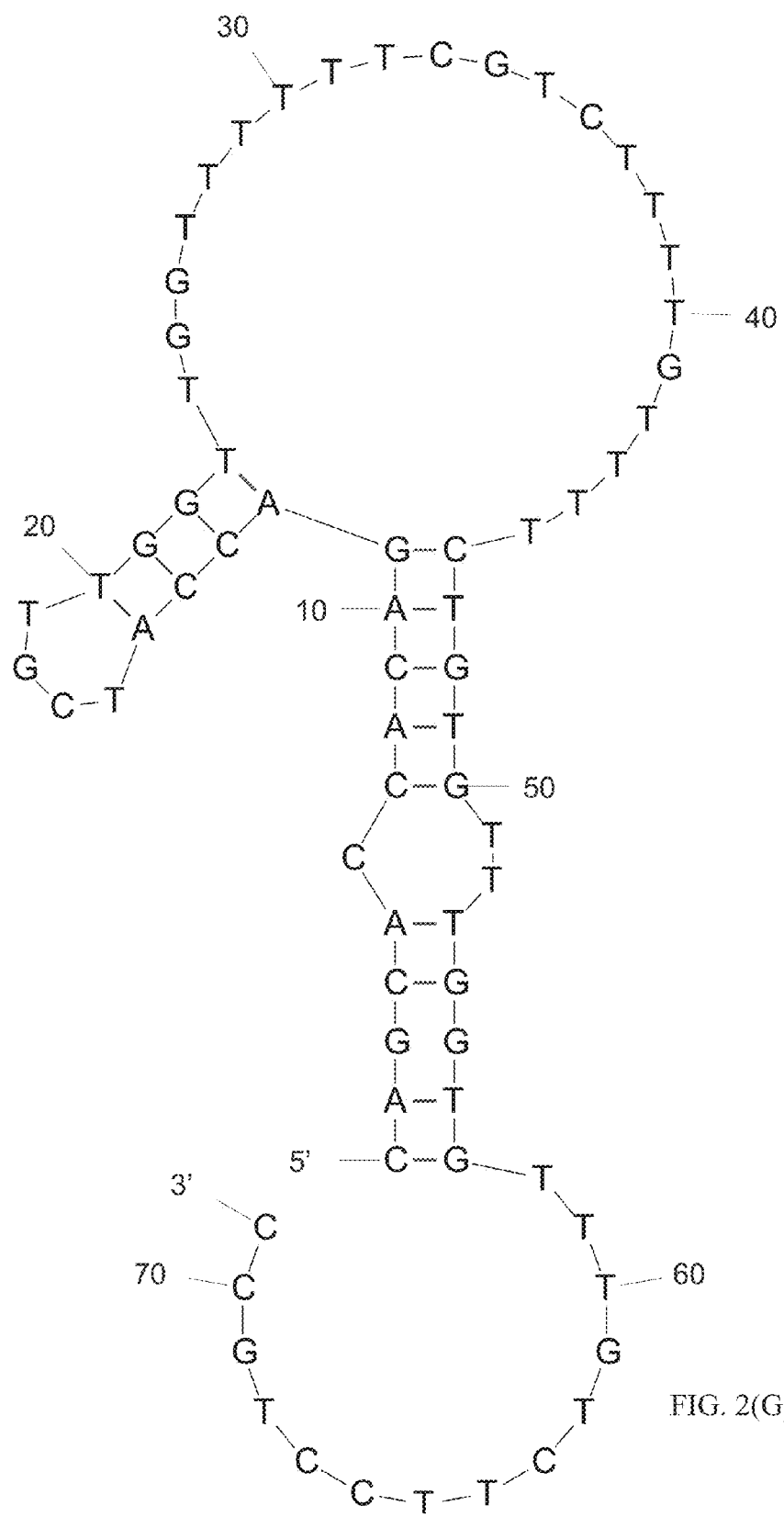
Figure 2H:
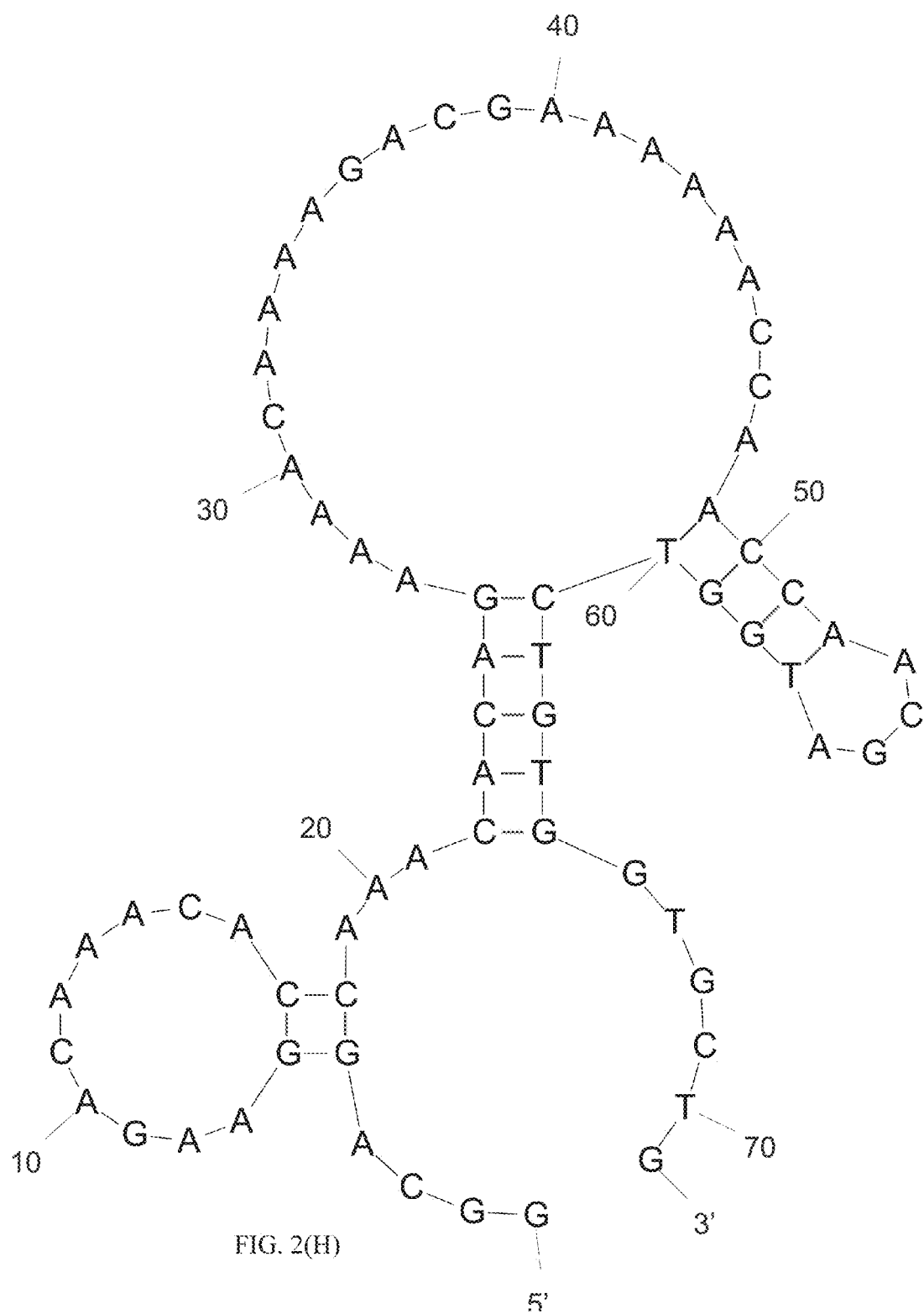
Figure 2I:
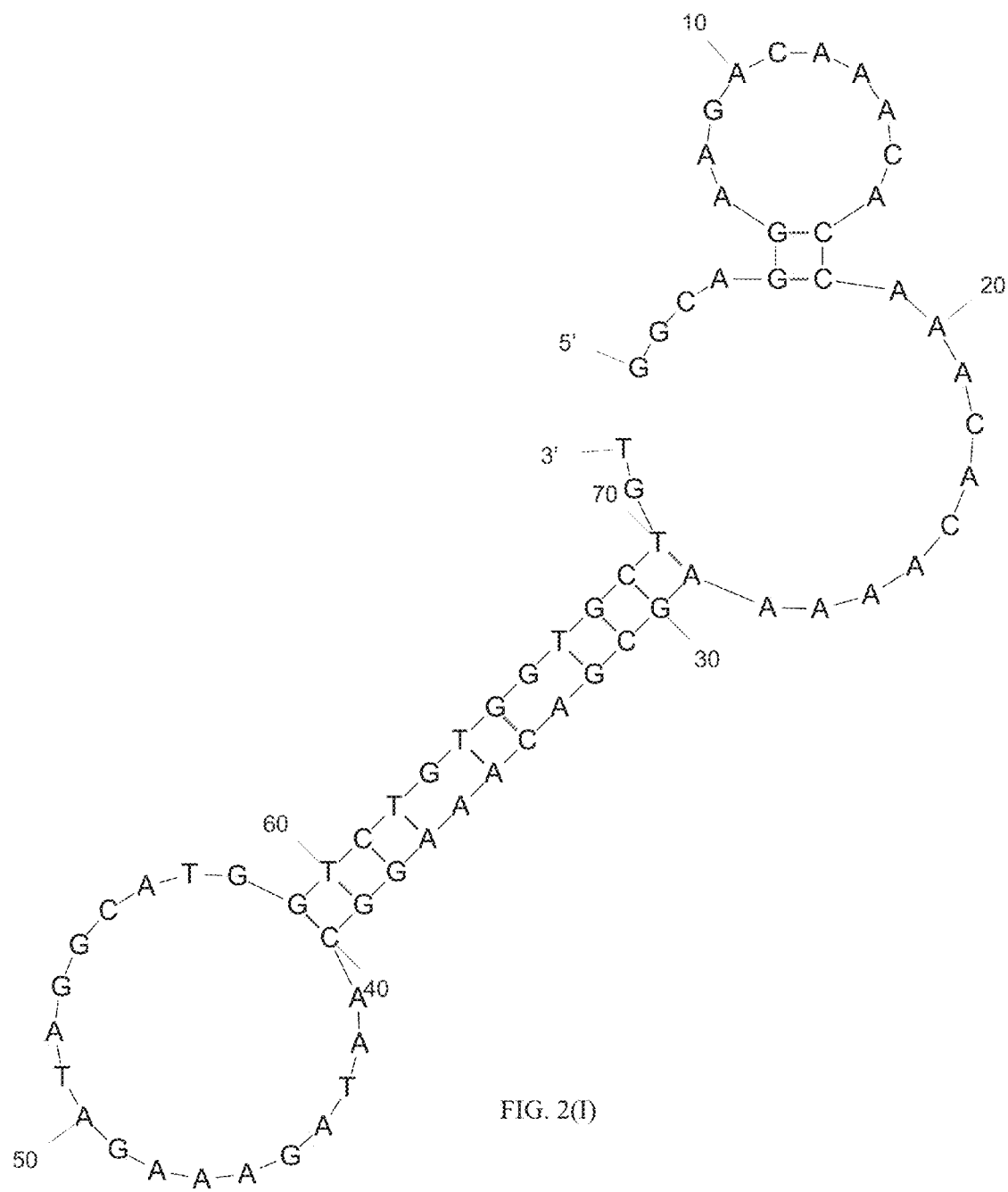
Figure 2J:
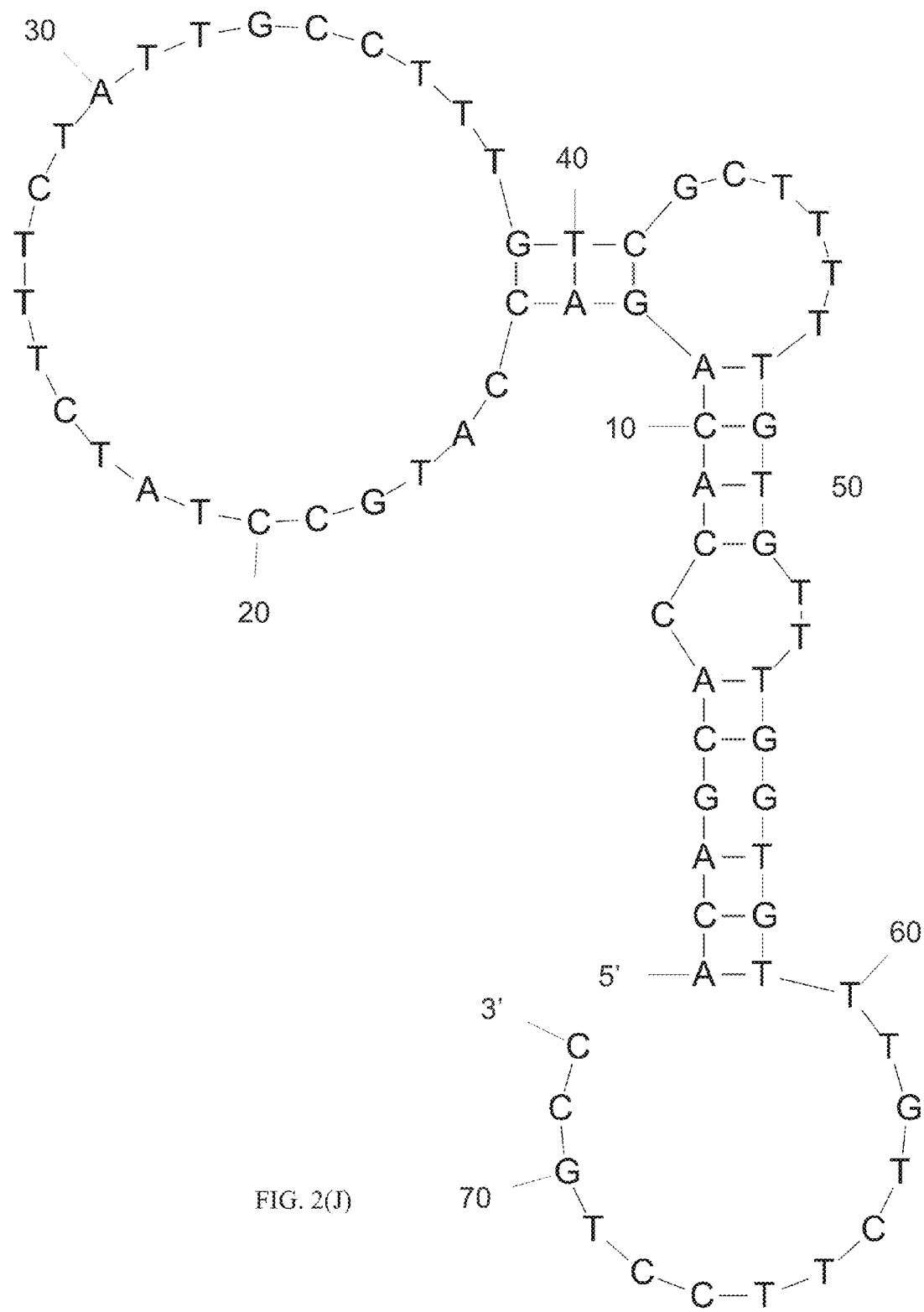
Figure 2K:
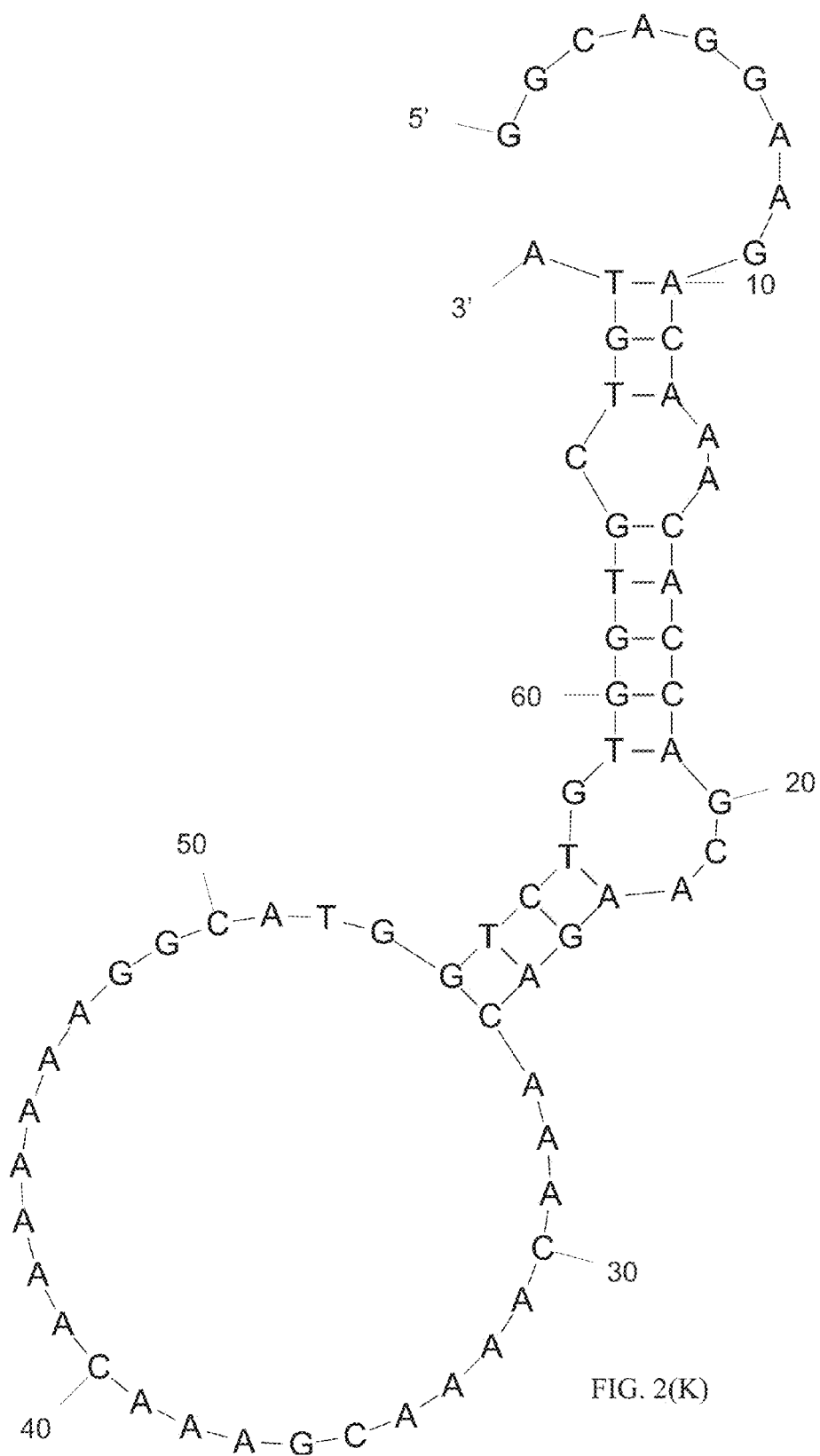
Figure 2L:
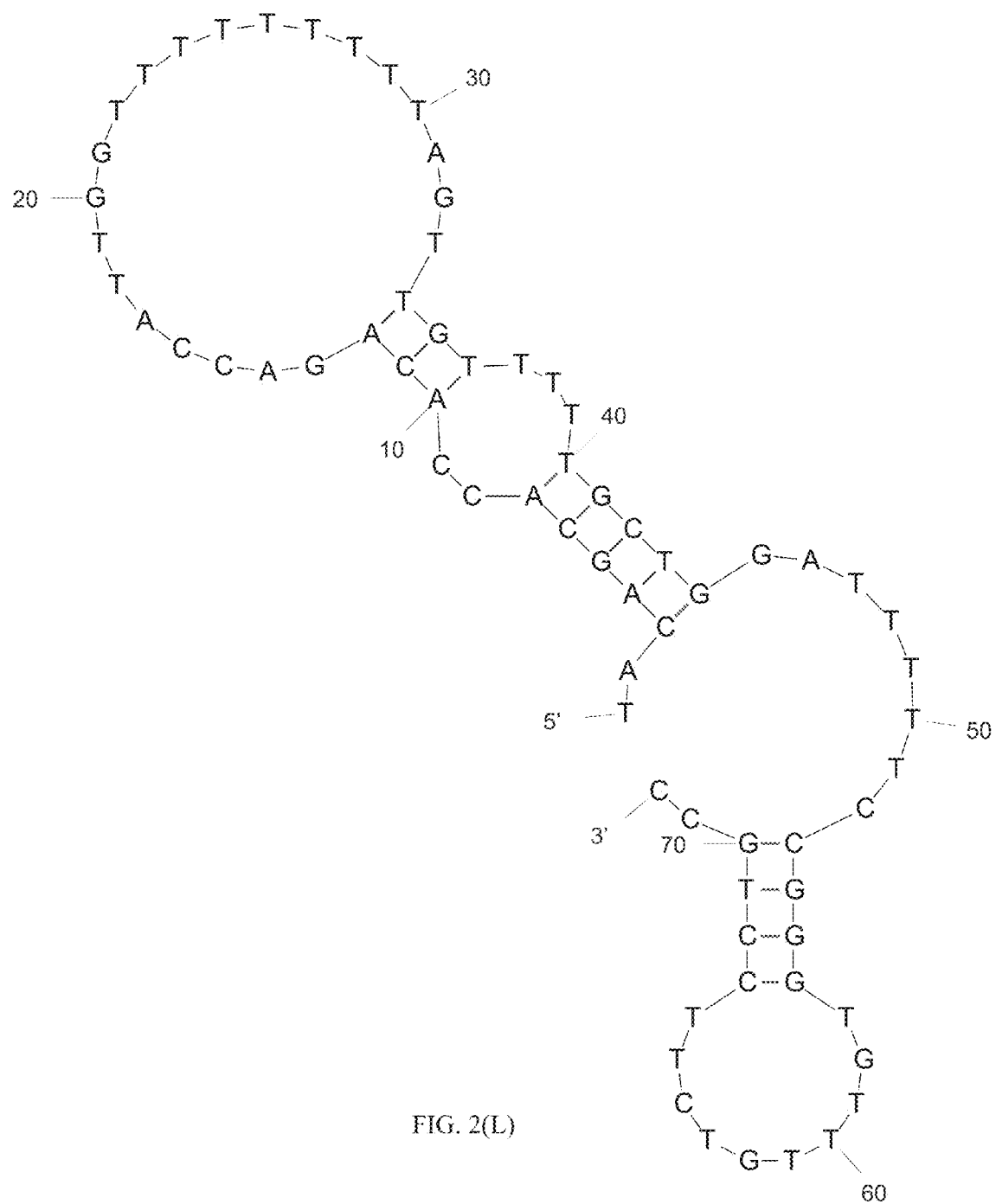
Figure 2M:
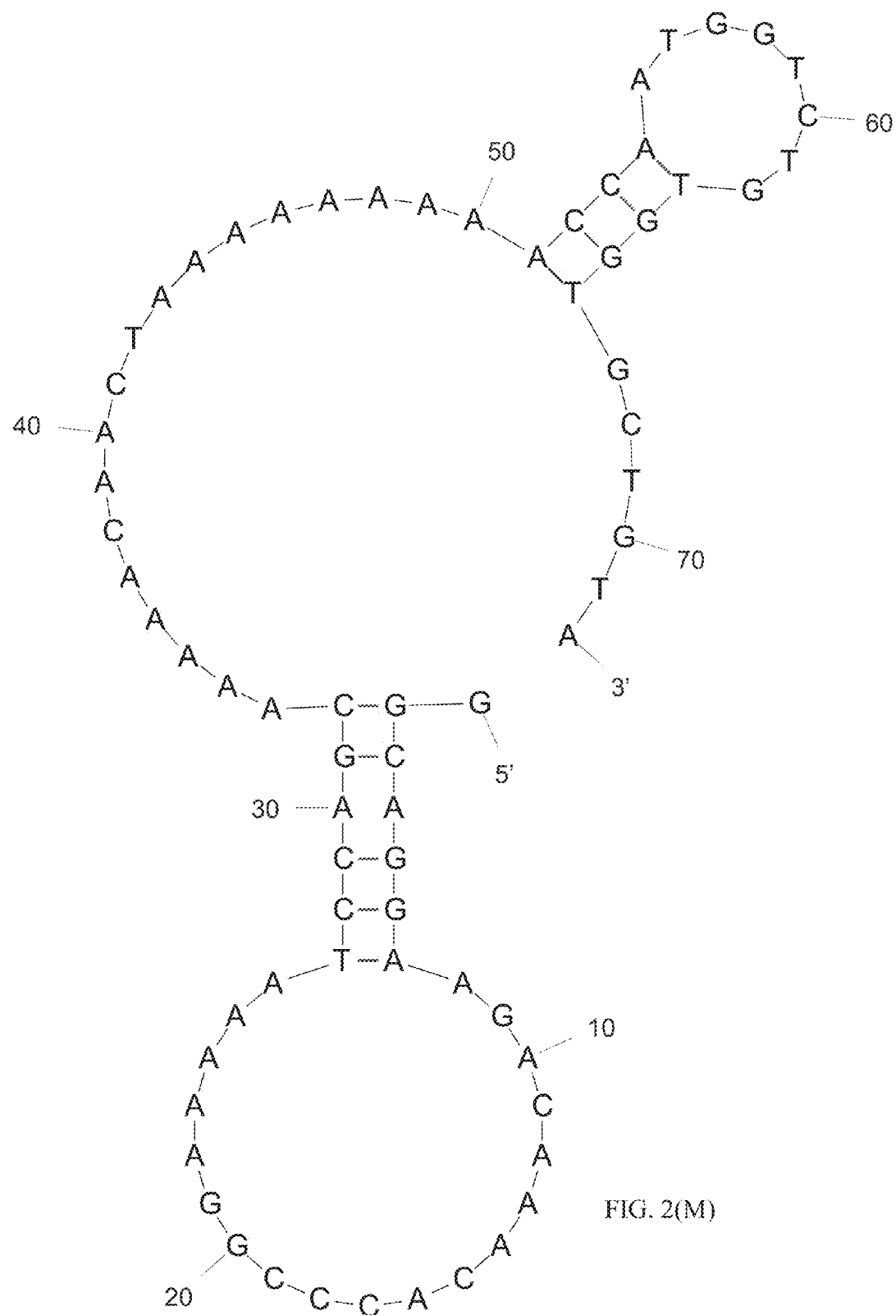

The present invention provides aptamers bind specifically to different histologically-classified ovarian cancer cell, which are selected in vitro using systematic evolution of ligands by exponential enrichment (SELEX) and microfluidic chip technology. The aptamers of the present invention exhibit high binding affinity to different histologically-classified ovarian cancer cells. Furthermore, a label, for instance, a fluorescence label, is conjugated to the aptamers specific for different histologically-classified ovarian cancer cells of the present invention for the detection of signals, such as fluorescence signals, in immunoassay to verify the high specificity to different histologically-classified ovarian cancer of the aptamers of the present invention. The specificity to other non-ovarian cancer cell of the aptamers of the present invention is low. Hence, the aptamers of the present invention can not only be used for rapid detection of ovarian cancer cell but can also be used for recognition of ovarian cancer cells according to their histological classifications. Due to high specificity and stability, the aptamers of the present invention are ideal serum tumor markers for early-stage ovarian cancer detection.

Definition

As used herein, the terms "polynucleotide", "nucleic acid", "nucleic acid molecule", "nucleic acid sequence", "polynucleotide sequence", "nucleotide sequence", and "bases sequence" are interchangeable to refer to polymeric forms of nucleotides of any length. The polynucleotides can comprise deoxyribonucleotides, ribonucleotides, and/or their analogs or derivatives. Nucleotide sequences shown herein are listed in the 5' to 3' direction.

An aptamer is "specific for" ovarian cancer cells, or more specifically, various histologically-classified ovarian cancer cells, when the aptamer binds to or interact with such ovarian cancer cells but does not bind to or interact significantly with other type of cancer cells.

As used herein, the terms "microfluidic device," "integrated microfluidic device," and "microfluidic chip," are used interchangeably to refer to a single integral unit that has a microfluidic reactor, microfluidic flow channels, and valves. Microfluidic devices typically also have other microfluidic components, such as pumps, columns, mixers, and the like. Most often the chip is fabricated from elastomer, glass, or silicon. Typically, the chip is box-shaped with a height that is relatively small compared to length and width; however, the chip can have other shapes including cubical, cylindrical, and others.

As used herein, the term "antibody" includes but not limited to a polypeptide or a polypeptide fragment substantially encoded by immunoglobin which specifically binds to an analyte (antigen).

A "sample" is any biological sample derived from a subject, patient. The term includes, but is not limit to, biological fluids such as blood, serum, plasma, urine, cerebrospinal fluid, tears, saliva, laryngeal epithelial cells, sputum, lymph, dialysis fluid, lavage fluid, and other liquid samples, as well as cell and tissues of biological origin. The term also includes cells or cells derived therefrom and the progeny thereof, including cells in culture, cell supernatants, and cell lysates. It further includes organ or tissue culture-derived fluids, tissue biopsy samples, tumor biopsy samples, stool samples, and fluids extracted from physiological tissues, as well as cells dissociated from solid tissues, tissue sections, and cell lysates. This definition encompasses samples that have been manipulated in any way after their procurement, such as by treatment with reagents, solubilization; or enrichment for certain components, such as polynucleotides or polypeptides. Also included in the term are derivatives and fractions of patient samples. A patient sample may be used in a diagnostic or other monitoring assay.

SELEX Microfluidic Chip

A SELEX microfluidic chip is used to automatically perform SELEX for the in vitro selection of ovarian cancer cell-specific aptamers of the present invention. The SELEX microfluidic chip of the present invention is made of two layers of polydimethylsiloxane (PDMS, Sylgard 184A/B, Dow Corning Corp., USA) and a glass layer (G-Tech Optoelectronics Corp., Taiwan).

Single-strand DNA (ssDNA) Library, Primers, Reagents, and Operational Conditions of Polymer Chain Reaction (PCR)

The ssDNA library was obtained from Medclub Scientific Co., Ltd., Taiwan, which was synthesized and purified to a final concentration of 1 μM. Each ssDNA sequence of the library was made of a total of 72 base pairs with a central region of 40 random nucleotide bases flanked by 2 specific 16-base primer sequence that function as primer-binding sites for the subsequent PCR process.

A washing buffer solution containing 1 L of Dulbecco's phosphate-buffered saline (DPBS, Invitrogen Co., USA), 4.5 g of glucose and 5 mL of 1 M $MgCl_2$, was prepared and stored at 4° C. prior to use.

A binding buffer solution was made of 1 L of DPBS, 4.5 g of glucose, 100 mg transfer ribonucleic acid, 1 g bovine serum albumin and 5 mL of 1 M $MgCl_2$, and was stored at 4° C. prior to use.

Fore each selection round, 300 μL of the washing buffer solution was used for the washing process and 50 μL of the binding buffer solution was used for incubation of the ssDNA with the cell-magnetic bead complexes.

The PCR reagents contained 0.5 μL of the forward primer (5'-GGCAGGA AGACAAACA-3', SEQ ID NO: 27, 0.5 μM), 0.5 μL of the reverse primer (5'-ACAGCACCACA-GACCA-3', SEQ ID NO: 28, 0.5 μM), 0.5 μL of deoxy-nucleotide triphosphates (dNTPs, 0.2 mM), 2 μL of ssDNA (0.1 μM), 0.125 μL of Taq DNA polymerase (New England Biolabs Co., Ltd., Taiwan), and then double-distilled water ($ddH_2O$) was added to make a total volume to 25 μL.

The PCR process was performed with an initial denaturation at 94° C. for 10 minutes, followed by 20 cycles of denaturation at 94 for 30 sec, annealing at 63° C. for 15 seconds, and extension at 72° C. for 30 seconds. A final extension step at 72° C. for 10 minutes was carried out following the last cycle. After five rounds of Cell-SELEX screening, the PCR products from the fifth round (R5) were purified and cloned using the TOPO TA Cloning kit (Invitrogen, USA).

Cell Culture and Preparation of Magnetic Beads

In one embodiment of the present invention, TOV21G cell line was used to serve as the target cell for clear-cell type ovarian cancer cell; TOV112D and IGROV1 cell lines were both used to serve as the target cells for endometrioid-cell type ovarian cancer cell; BG-1 cell line was used to serve as the target cell for serous-cell type ovarian cancer cell. All the cell lines above were obtained from the Department of Obstetrics and Gynecology, National Cheng Kung University, Taiwan. The TOV112D, IGROV1 and TOV-21G cell lines were cultured in a RPMI-1640 medium (Invitrogen Co., USA) and the BG-1 cell line was cultured in Dulbecco's Modified Eagle's Medium/F12 (DMEM/F12, Invitrogen Co., USA).

MCF7, a breast cancer cell line, and NIH3T3, a mouse embryonic fibroblast cell line, were provided from The Institute of Microbiology and Immunology, Chung Shan Medical University, Taichung, Taiwan; HeLa, a cervical cancer cell line, A549, a lung cancer cell line, and HepG2, a liver cancer cell line, were provided from The Institute of Biomedical Sciences, National Sun Yat-Sen University, Kaohsiung, Taiwan; M2-B104 (BCRC number: 60228), a mouse neuroblastoma cell line, was provided from The Food Industry Research Development Institute, Hsinchu, Taiwan. All of the above cell lines were cultured in DMEM (Invitrogen Co., USA) and were incubated at 37° C. in a 5% $CO_2$ atmosphere. All media were supplemented with 10% fetal bovine serum (Invitrogen Co., USA) and 100 UI/mL penicillin-streptomycin (Invitrogen Co., USA).

The Dynabeads® Epithelial Enrich immunomagnetic beads (EpiEnrich, $4\times10^8$ beads/mL, Ø=4.5 μm, Invitrogen Co., USA) were used to form the target cell-bead complexes or control cell-bead complexes for the Cell-SELEX selection process. 100 μL of the EpiEnrich immunomagnetic beads were firstly washed in 1 mL of a 1×phosphate-buffered saline buffer (PBS, Merck Ltd., Darmstadt, Germany) twice, and then were re-suspended into a 1×PBS buffer with a total volume of 1 mL. Next, the cells were mixed with the binding buffer solution with a total volume of 1 mL. This was followed by loading the mixture into a test tube pre-loaded with 10 μL of EpiEnrich immunomagnetic beads. Cell-bead complexes were counted to be $1\times10^5$ cells/100 μL for the Cell-SELEX selection process. The binding ratios were also verified by microscope-based measurements.

For testing the binding selectivity between the screened aptamer and the cancer cell lines, an aptamer-magnetic bead was also prepared. First, 100 μL of MyOne™ magnetic beads with the carboxylic acid functional group (Dynabeads® MyOne™ Carboxylic Acid, $6.17\times10^7$ beads/mL, Ø=1.0 μm, Invitrogen Co., USA) were transferred to a test tube, then placed in a magnetic field, and the resulting supernatant was discarded. The beads were washed twice with $ddH_2O$, and the resulting supernatant was again discarded. Then, $ddH_2O$, amine modified aptamer (100 μM) and N-(3-Dimethylaminopropyl)-N'-ethylcarbodiimide hydrochloride (EDAC, 120 mg/mL, Sigma Co., USA) were added and incubated for 18 hours at room temperature without light exposure. After 18 hours, a magnetic field was applied to collect the beads and the supernatant was discarded. After repeating the washing step twice with 1 mL of 0.02% Tween 20 (Sigma Co., USA) and 0.1% of sodium dodecyl sulfate (SDS, Sigma Co., USA), then ethanol amine (0.1 M, Sigma Co., USA) was used to block the free uncoupled sites on the surface of the aptamer-magnetic beads at room temperature for one hour without light exposure. After blocking, the aptamer-magnetic beads were washed twice in 1 mL $ddH_2O$ and re-suspended in 1 mL $ddH_2O$ and was stored at 4° C. prior to use.

Procedure of SELEX Selection for Aptamers Using Microfluidic Chip System

As shown in FIG. 1, the flow chart of SELEX selection of aptamers specific for ovarian cancer cells using a microfluidic chip in conjunction with magnetic beads according to the present invention, firstly, a random library of ssDNA sequences and target cells coated with magnetic beads (the target cell-magnetic bead complex) were loaded together into a reaction chamber and incubated for the positive selection, FIG. 1 step (A). The ssDNA sequences with high affinity to the target cell would then bind to the target cell-magnetic bead complex, forming a ssDNA-magnetic bead-target cell complex. Then, an external magnetic field was applied to collect the ssDNA conjugated to the target cell-magnetic bead complexes, whereas any unbound ssDNA was flushed away with the washing buffer solution by a micropump, as shown in FIG. 1 step (B). Next, as shown in FIG. 1 step (C), the target cells were heated and thermally lysed to release the bound ssDNA with high affinity to the target cells. The released ssDNA sequences were then transported into another reaction chamber pre-loaded with control cells coated with magnetic beads to exclude ssDNA sequences via a negative selection process, as shown in FIG. 1 step (D). Similarly, a magnetic field was applied to collect any ssDNA conjugated to the control cell-magnetic bead complexes. After the negative selection process, since the ssDNA sequences specific to the target cell would not bound to the control cells, the unbound ssDNA sequences present in the supernatant were collected as aptamers with high specificity to the target cells, as shown in FIG. 1 step (E). Then, as shown in FIG. 1 step (F), a PCR process was performed to amplify these selected aptamers with high specificity to the target cells. Finally, the PCR products, which were the results from the first round (R1) of the SELEX selection process, were transported back to the reaction chamber for the next round of selection, as shown in FIG. 1 step (G). All the above steps of the SELEX selection process were carried out by an automated microfluidic system.

During the SELEX selection process, in turn, one histologically-classified ovarian cancer cell, such as TOV21G, IGROV1, or BG-1, etc, served as the target cell while the others served as the control cells respectively. The SELEX selection process can rapidly, automatically, and accurately select high affinity aptamers specific for different hitologically-classified ovarian cancer cells.

EXAMPLE 1

Selection of Aptamers Specific to Different Histologically-classified Ovarian Cancer Cells The concentrations of ssDNA from different rounds of selection were determined by using an ultraviolet-visible wavelengths spectrophotometer (NanoPhotometer® P-Class, Implen GmbH, GER) and were then adjusted to a concentration of 50 ng/2 µL for further PCR amplification. During this PCR process, 5'-Cy5 fluorescence-dye-modified primers (Protech Co., Ltd., Taiwan.) were used for PCR amplification. After attaching the Cy5 probe via PCR, the spectrophotometer was used again to determine the concentration of PCR products with the Cy5 probe from the different rounds of enriched ssDNA. The Cy5 probe attached ssDNA were then adjusted to 500 ng/50 µL for the flow cytometric analysis when binding with TOV21G, TOV112D, IGROV1, and BG-1 cell lines, respectively. The fluorescence was determined by flow cytometry (BD Accuri™ C6, Becton, Dickinson and Company, USA). All of experiments were repeated three times.

For performing the binding assay, $1\times10^5$ ovarian cells with different histologically classifications, including BG-1, TOV112D, IGROV1 and TOV-21G were incubated in 200 µL of binding buffer solution with ssDNA aptamers selected from the first round to the fifth round, respectively, from the Cell-SELEX selection for 30 minutes at room temperature. The cells were then manually washed with 50 µL of washing buffer solution followed by incubation in a micro-mixer for 1 minute. After washing, this step was repeated for another five times. Finally, the ssDNA bound cells were analyzed using flow cytometry. The relative ssDNA-binding capability of different histologically-classified ovarian cancer cells to the selected aptamers versus the entire ssDNA library could be determined by comparing the results obtained from round one (R1) to round five (R5).

The selected ssDNA sequences from each round of Cell-SELEX selection, R1 to R5, were amplified using PCR. After the PCR amplification, the selected sequences were collected and analyzed in a flow cytometer to confirm the enrichment of ssDNA sequences via binding to specific histologically-classified ovarian cancer cells. When the selected ssDNA sequences were specifically enriched and bound to only one specific histologically-classified ovarian cancer cell line, the fluorescence intensity was observed to increase from R1 to R5. For the TOV21G cell line, the fluorescence signal of the selected ssDNA sequences in the fourth and the fifth rounds increased dramatically to $10^5$ arbitrary units (a.u.) when compared to the first round (at about $10^4$ a.u.). For TOV112D cell line, the fluorescence signal of the selected ssDNA sequences in the fifth round also increased from $10^4$ a.u. to $10^5$ a.u. Similarly, the fluorescence signals of the selected ssDNA pools for BG-1 and IGROV1 also increased from the first to the fifth round. In the present invention, quantitative fluorescence signal measurements were used instead of traditional electrophoresis gel analysis since electrophoresis gel analysis can only semi-quantitatively measure the binding efficiency of the specific aptamers. According to the results of the present invention, only five rounds of SELEX selection is required because the intensity of the fluorescence signal remained steady between the fourth and the fifth round. Thus, after five rounds of SELEX selection, the PCR products obtained from the fifth round were cloned using a TOPO TA cloning kit.

For the present invention, twenty aptamer sequences for each histologically-classified ovarian cancer cell line (in a total of 80 sequences) were chosen randomly for the competitive test to determine their affinity.

In the competitive test, free target cells were used as competitors for the aptamers from the SELEX selection above against the epithelial enriched magnetic beads coated with our without target cells. Firstly, a "negative assay" was performed, in which the epithelial enriched magnetic beads not coated with target cells was incubated with the aptamers. Since only few aptamers would bind to such epithelial enriched magnetic beads not coated with target cells, only a weak or no PCR signal could be observed after PCR amplification. Then, the competitive test was performed by incubating free target cells, epithelial enriched magnetic beads coated with target cells (target cell-magnetic bead complex), and aptamers. Although a proportion of the aptamers would bind to the free target cells, they could not be collected when a magnetic field was later applied. Therefore, a weak PCR signal was observed accordingly after PCR amplification. Finally, a "positive assay" was performed, in which the target cell-magnetic bead complexes and aptamers were incubated together, and since all aptamers would bind to the target cell-magnetic bead complexes, it was expected to observe a strong PCR signal after PCR amplification.

After the competitive test as described above, high affinity aptamers were selected, including: five TOV21G-specific aptamers (SEQ ID NO: 14, SEQ ID NO: 15, SEQ ID NO: 16, SEQ ID NO: 17, and SEQ ID NO: 23), four TOV112D-specific aptamers (SEQ ID NO: 18, SEQ ID NO: 19, SEQ ID NO: 20, and SEQ ID NO: 21), three BG-1-specific aptamers (SEQ ID NO: 23, SEQ ID NO: 25, and SEQ ID NO: 26), and three IGROV1-specific aptamers (SEQ ID NO: 22, SEQ ID NO: 23, and SEQ ID NO: 24). Particularly, SEQ ID NO: 23 was identified to be specific to TOV21G, BG-1, and IGROV1. All aptamers specific to different histologically-classified ovarian cancer cells hereinbefore were further subject to DNA sequencing and synthesis (Medclub Scientific Co., Taoyuan, Taiwan). The sequence of each aptamer is shown in Table 1 as follow:

TABLE 1

| Ovarian cancer cell type | Aptamer | bp | Aptamer sequence, 5'-3' |
|---|---|---|---|
| Clear cell-type ovarian cancer cells | SEQ ID NO: 14 | 72 | GGCAGGATTACAAACACCAAAAGAAGCACGAACAAAAAAAACAAGGAAACACTACTTGGTCTGTGGTGCTGT |
| | SEQ ID NO: 15 | 72 | ACAGCACCACAGACCAAGTAGTGTTTCCTTGTTTTTTTTGTTCGTGCTTCTTTTGGTGTTTGTAATCCTGCC |
| | SEQ ID NO: 16 | 68 | TACAGCACCACAGACCACGTTTTTGTTCTTTTTGTTTGCTGTTGAGTTTTGGTGTTTGTCTTCCTGCC |

TABLE 1-continued

| Ovarian cancer cell type | Aptamer | bp | Aptamer sequence, 5'-3' |
|---|---|---|---|
| | SEQ ID NO: 17 | 68 | GGCAGGAAGACAAACACCAAAACTC AACAGCAAACAAAAAGAACAAAAAC GTGGTCTGTGGTGCTGTA |
| | SEQ ID NO: 23 | 72 | ACAGCACCACAGACCATGCCTATCT TTCTATTGCCTTTGTCGCTTTTTGT GTTTGGTGTTTGTCTTCCTGCC |
| Endometrioid-cell type ovarian cancer cell | SEQ ID NO: 18 | 65 | GGCAGGAAGACAAACACGCACTGGC AGGAAGACAAACACGGGACGTTGGT GGTCTGTGGTGCTGT |
| | SEQ ID NO: 19 | 72 | GGCAGGAAGACAAACACCAAGAGCG AGAGAAGAAAACCGGGAAAAGGACA ACTAGCTGGTCTGTGGTGCTGT |
| | SEQ ID NO: 20 | 71 | CAGCACCACAGACCATCGTTGGTTG GTTTTTTCGTCTTTTGTTTTCTGTG TTTGGTGTTTGTCTTCCTGCC |
| | SEQ ID NO: 21 | 71 | GGCAGGAAGACAAACACCAAACACA GAAAACAAAAGACGAAAAAACCAAC CAACGATGGTCTGTGGTGCTG |
| | SEQ ID NO: 22 | 72 | GGCAGGAAGACAAACACCAAACACA AAAAGCGACAAAGGCAATAGAAAGA TAGGCATGGTCTGTGGTGCTGT |
| | SEQ ID NO: 23 | 72 | ACAGCACCACAGACCATGCCTATCT TTCTATTGCCTTTGTCGCTTTTTGT GTTTGGTGTTTGTCTTCCTGCC |
| | SEQ ID NO: 24 | 68 | GGCAGGAAGACAAACACCAGCAAGA CAAACAAAACGAAACAAAAAAGGC ATGGTCTGTGGTGCTGTA |
| Serous-cell type ovarian cancer cell | SEQ ID NO: 23 | 72 | ACAGCACCACAGACCATGCCTATCT TTCTATTGCCTTTGTCGCTTTTTGT GTTTGGTGTTTGTCTTCCTGCC |
| | SEQ ID NO: 25 | 72 | TACAGCACCACAGACCATTGGTTTT TTTTTAGTTGTTTTTGCTGGATTTT TCCGGGTGTTTGTCTTCCTGCC |
| | SEQ ID NO: 26 | 72 | GGCAGGAAGACAAACACCCGGAAAA ATCCAGCAAAAACAACTAAAAAAAA ACCAATGGTCTGTGGTGCTGTA |

The secondary structures of these selected aptamers at 25° C. were further predicted using MFOLD software (version 3.5) and are shown in FIG. 2.

For the above aptamers, the sequences specific for different histologically-classified ovarian cancer cells thereof were further evaluated and are listed in Table 2 as follow:

TABLE 2

| Ovarian cancer cell type | bp | Specific binding sequences, 5'-3' |
|---|---|---|
| Clear cell-type ovarian cancer cells | 41 | CCAAAAGAAGCAC-GAACAAAAAAACAAGGAA ACACTACTT (SEQ ID NO: 1) |
| | 41 | AAGTAGTGTTTCCTTGTTTTTTTGT-TCGTGC TTCTTTTGG (SEQ ID NO: 2) |
| | 35 | ACGTTTTTGTTCTTTTTGTTGCTGTT-GAGTTT TGG (SEQ ID NO: 3) |
| | 36 | CCAAAACTCAACAG-CAAACAAAAAGAACAAAA ACGT (SEQ ID NO: 4) |
| | 41 | ATGCCTATCTTTCTATTGCCTTT-GTCGCTTTT TGTGTTTGG (SEQ ID NO: 10) |
| Endometrioid-cell type ovarian cancer cell | 34 | CGCACTGGCAGGAAGA-CAAACACGGGACGTTG GT (SEQ ID NO: 5) |
| | 41 | CCAAGAGCGAGAGAAGAAAAC-CGGGAAAGGA CAACTAGCT (SEQ ID NO: 6) |

TABLE 2-continued

| Ovarian cancer cell type | bp | Specific binding sequences, 5'-3' |
|---|---|---|
| | 41 | ATCGTTGGTTGGTTTTTTCGTCTTTT-GTTTTC TGTGTTTGG (SEQ ID NO: 7) |
| | 41 | CCAAACACAGAAAACAAAAGAC-GAAAAAACCA ACCAACGAT (SEQ ID NO: 8) |
| | 41 | CCAAACACAAAAAGCGACAAAGGCAATA-GAAA GATAGGCAT (SEQ ID NO:9) |
| | 41 | ATGCCTATCTTTCTATTGCCTTT-GTCGCTTTT TGTGTTTGG (SEQ ID NO: 10) |
| | 36 | CCAGCAAGACAAACAAAAC-GAAACAAAAAAAG GCAT (SEQ ID NO: 11) |
| Serous-cell type ovarian cancer cell | 41 | ATGCCTATCTTTCTATTGCCTTT-GTCGCTTTT TGTGTTTGG (SEQ ID NO: 10) |
| | 40 | ATTGGTTTTTTTTTAGTTGTTTTTGCTG-GATT TTTCCGGG (SEQ ID NO: 12) |
| | 40 | CCCGGAAAAATCCAG-CAAAAACAACTAAAAAA AAACCAAT (SEQ ID NO: 13) |

EXAMPLE 2

Dissociation Constant

In order to determine the binding affinities of the selected aptamers to different histologically-classified ovarian cancer cells, various concentrations of carboxyfluorescein (FAM) labelled aptamers ranging from 500 nM to 0.1 nM were incubated with BG-1, TOV112D, IGROV1 and TOV-21G ($1\times10^5$ cells for each), respectively, for 15 minutes in 50 μL of the binding buffer solution. Then, cells were washed six times by 50 μL of the washing buffer solution, and then suspended in 50 μL the binding buffer solution for analysis using a flow cytometry. A sample containing solely the cell was used as control group. The resulting fluorescence intensity of the aptamers was further used to calculate the equilibrium dissociation constant ($K_d$). $K_d$ of the fluorescent aptamer was obtained by using Prism software (GraphPad Software, Inc. USA) and was then constructed into a plot of the mean fluorescence intensity of the specific binding intensity (Y) versus the aptamer concentration (X), $Y=B_{max}X/(K_d+X)$.

For determining the dissociation constant, $K_d$, of the selected aptamers and their binding affinity to specific target cells, the selected aptamers were modified by FAM fluorescence label, prepared in various concentrations, and analyzed. The $K_d$ of the selected aptamers is between 1.8 to 201.3 nM; thus, is obviously superior to most antibodies ($K_d=10^{-7}$-$10^{-9}$ nm). More specifically, for TOV112D cell line, SEQ ID NO: 19 exhibits the best binding affinity with $K_d$ of 22.4 nM; for BG-1 cell line, SEQ ID NO: 26 exhibits the best binding affinity with $K_d$ of 1.3 nM; for IRGOV1 cell line, SEQ ID NO: 23 exhibits the best binding affinity with $K_d$ of 10.2 nM.

EXAMPLE 3

Binding Assay of Selected Aptamers with Different Histologically-Classified Ovarian Cancer Cells $1\times10^5$ of different histologically-classified ovarian cancer cells, including BG-1, TOV112D, IGROV1, and TOV-21G were gently washed with 1×PBS followed by re-suspending in 200 μL of binding buffer solution and incubation with an addition of 50 μL of 250 nM FAM-labeled aptamers for 30 minutes. After incubation, the FAM-labeled aptamers were washed three times with 1× PBS, fixed in ice-cold 4% paraformaldehyde for 5 minutes, and air-dried for 5 minutes. Subsequently, the cells were placed on microscope slides with ProLong® Gold Antifade Reagent (Invitrogen Corporation, USA). The slides were then optically analyzed using a set of components including one collimation lens, one objective lens (Nikon LU Plan 10x/0.30 A, Nikon, Japan), three fluorescence filters (Nikon G-2A, Nikon, Japan), and a mercury lamp (MODEL C-SHG1, Nikon, Japan). Images of apatmer fluorescence were captured using a DS-Qi1Mc camera (1.5 megapixels, equipped with a Peltier cooling device and a programmable gain amplifier, Nikon, Japan) coupled to an inverted microscope equipped with a digital control module.

Figure 3A:
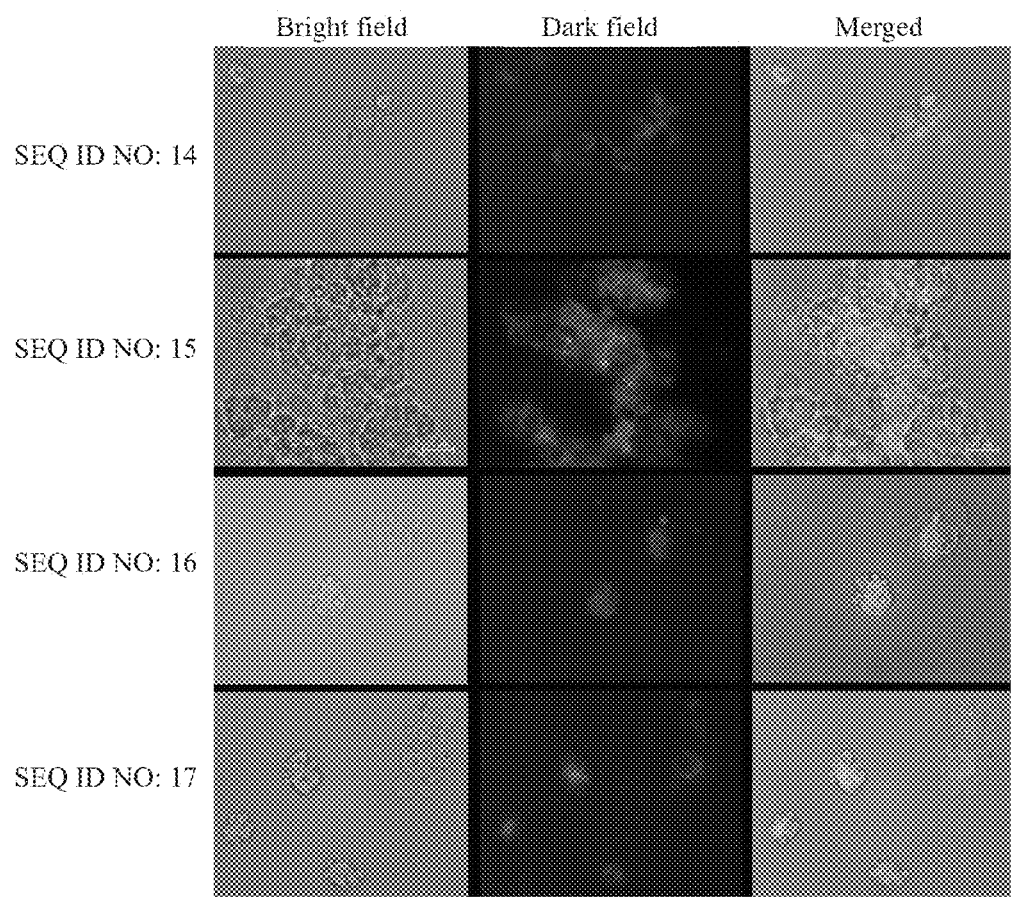
FIG. 3(A)-3(D), fluorescence images of the binding of the aptamers of the present invention to different histologically-classified ovarian cancer cells, wherein (A) indicates the binding of aptamers (SEQ ID NO: 14-17) to clear-cell type ovarian cancer cell TOV21G; (B)-(C) indicate the binding of aptamers (SEQ ID NO: 18-24) to endometrioid-cell type ovarian cancer cell TOV112D and IGROV1; (D) indicates the binding of aptamers (SEQ ID NO: 25-26) to serous-cell type ovarian cancer cell BG1.

As shown in FIG. 4, when the FAM-labeled aptamers of the present invention were used to substitute for antibodies in a traditional immunofluorescence assay for analyzing specific bindings to different histologically-classified ovarian cancer cells, significant fluorescent signals can be observed due to aptamers specifically binding to their corresponding target cells respectively. Meanwhile, the fluorescent signals revealed that the selected aptamers specifically bind to the surface of the target cells. As shown in FIG. 3(A), four aptamers specifically bind to TOV21G cells, including SEQ ID NO: 14, SEQ ID NO: 15, SEQ ID NO: 16, and SEQ ID NO: 17, wherein SEQ ID NO: 15 exhibits the strongest fluorescent signal among them due to its lowest $K_d$ of 1.8 nM, indicating the highest binding affinity to TOV21G cells. On the other hand, fluorescent signals are also observed beyond cell membrane, indicating that the aptamers specific to TOV21G cells are able to enter cells via diffusion or endocytosis.

Figure 3B:
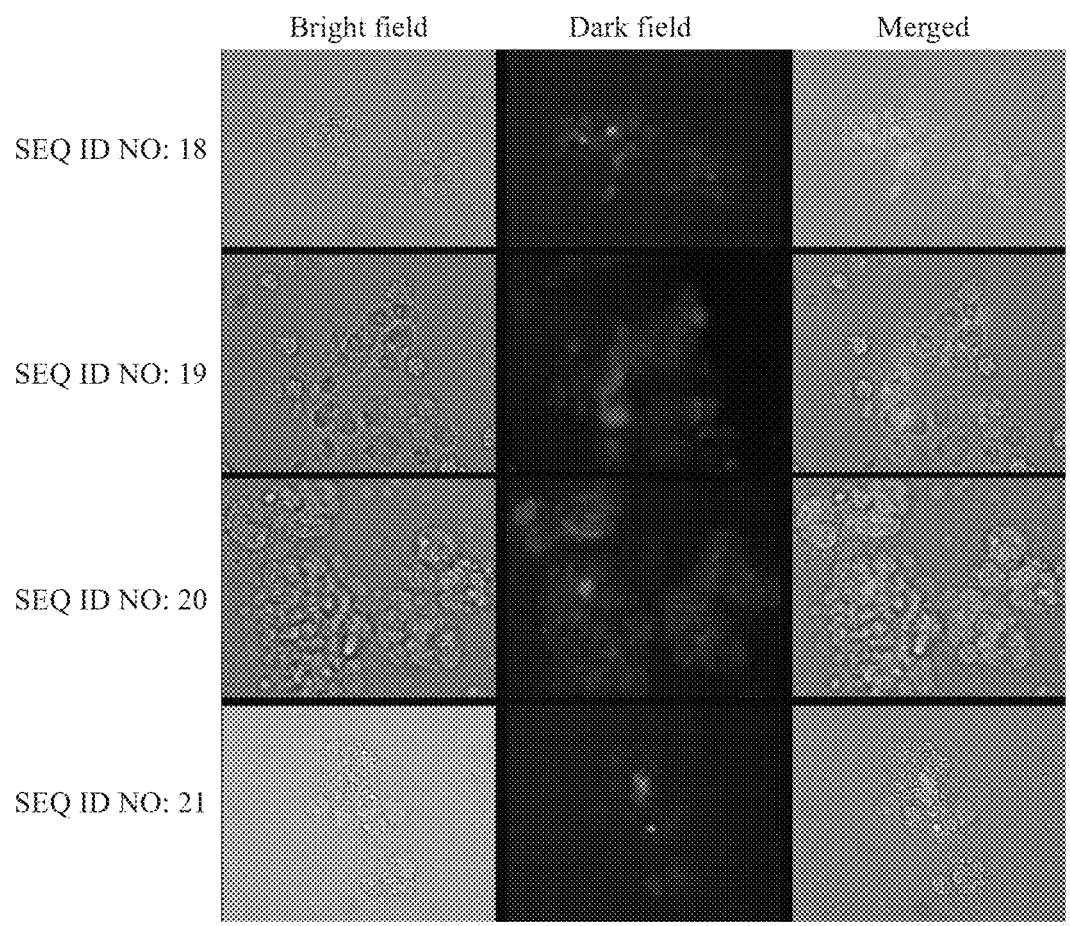
Figure 3C:
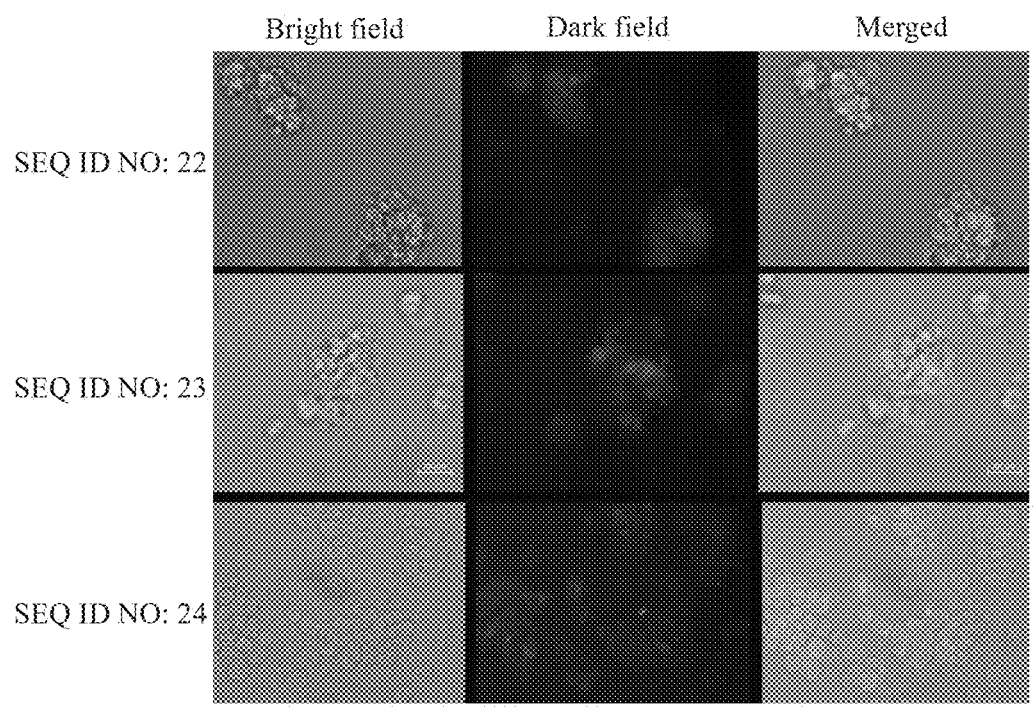

The binding affinities of the aptamers of the present invention to endometrioid-cell type ovarian cancer cell TOV112D and IGROV1 are illustrated in FIG. 3(B) and FIG. 3(C), in which SEQ ID NO: 19 and SEQ ID NO: 20 exhibit stronger fluorescent signals comparing with the two other TOV112D-specific aptamers due to their lower $K_d$ of 22.4 nM and 34.8 nM, respectively, indicating higher binding affinities to TOV112D cells. In particular, SEQ ID NO: 20 can clearly define the cell membrane region of the target cells, hence, is suitable for recognition of endometrioid-cell type ovarian cancer cells. Similarly, IGROV-1-specific aptamers are also suitable for recognition of endometrioid-cell type ovarian cancer cells. A proportion of fluorescent signal was observed from the cytoplasm indicating that the aptamers specific for TOV112D and IGROV-1 cells are able to be absorbed into the cells via diffusion or endocytosis.

Figure 3D:
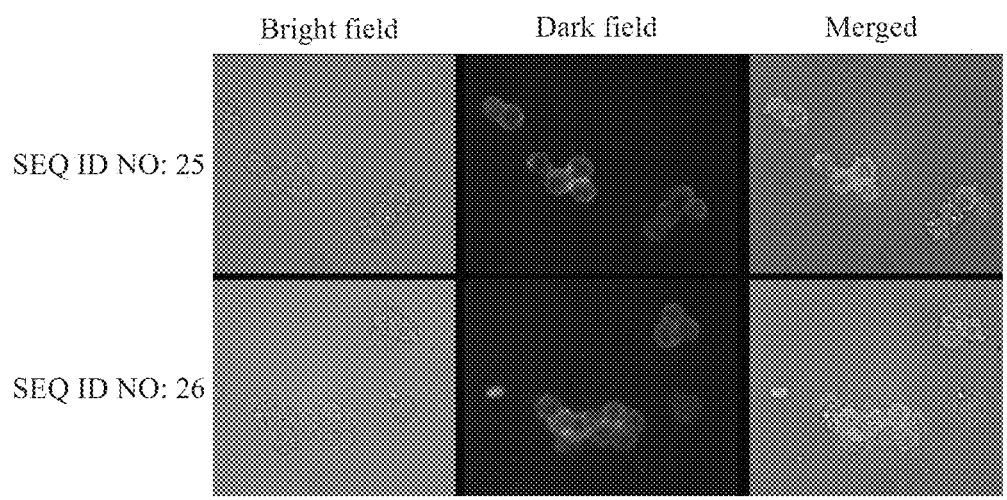

As shown in FIG. 3(D), both SEQ ID NO: 25 and SEQ ID NO: 26 clearly define the cell membrane region of serous-cell type ovarian cancer cell BG-1, indicating that both SEQ ID NO: 25 and SEQ ID NO: 26 bind specifically to the cell membrane of BG-1 cells, and as a result, the aptamers of the present invention can be used for the detection of serous-cell type ovarian cancer cells.

EXAMPLE 4

Binding Selectivity of the Aptamers of the Present Invention

The binding selectivity assay is to analyze the capture rate of the selected ovarian cancer-specific aptamers to various types of cancer cell lines. Firstly, different cancer cell lines ($1\times10^5$) and 10 μL of MyOne™ beads coated with ovarian cancer-specific aptamers were incubated together for 30 minutes and were added up to a final volume of 200 μL using the binding buffer solution. After incubation, the different cancer cell lines were then washed five times using 200 μL of the washing buffer solution followed by re-suspending in 200 μL of the binding buffer solution. Finally, the captured cells were counted using a hemocytometer under a microscope.

Such different cancer cell lines utilized to verify the specificity of the aptamer (10 ng) of the present invention to ovarian cancer cells include HeLa (cervical cancer cell line), MCF7 (breast cancer cell line), A549 (lung cancer cell line), HepG2 (liver cancer cell line), M2-B104 (mouse neuroblastoma cell line), and NIH3T3 (mouse embryonic fibroblast cell line).

As shown in Table 3, four TOV21G-specific aptamers (SEQ ID NO: 14-17) exhibit significantly high recognition (≥+++, ≥50.0% cell capture rate) toward their target cell, TOV21G, but relatively lower recognition to other cells (≤++, ≤49.9% cell capture rate). Similarly, four TOV112D-specific aptamers (SEQ ID NO: 18-21) and two BG-1-specific aptamers (SEQ ID NO: 25-26) exhibit high recognition (≥+++, ≥50.0% cell capture rate) towards their target cells, TOV112D and BG-1, respectively, but relatively lower recognition to other cells (≤++, ≤49.9% cell capture rate). For the three IGROV1-specific aptamers, only SEQ ID NO: 22 exhibits higher recognition (+++, 50.0-74.9% cell capture rate) towards IGROV1 and relatively lower recognition towards other cells. However, SEQ ID NO: 23 exhibits high recognition (+++, 50.0-74.9% cell capture rate) towards all three different histologically-classified ovarian cancer cells, indicating that it not only can be used to recognize endometrioid-cell type ovarian cancer cells but also is suitable for rapid but non-histological-specific ovarian cancer detection.

In Table 3, "+" refers to 0-24.9% cell capture rate; "++" refers to 25.0-49.9% cell capture rate; "+++" refers to 50.0-74.9% cell capture rate; "++++" refers to 75.0-100% capture rate.

Figure 4A:
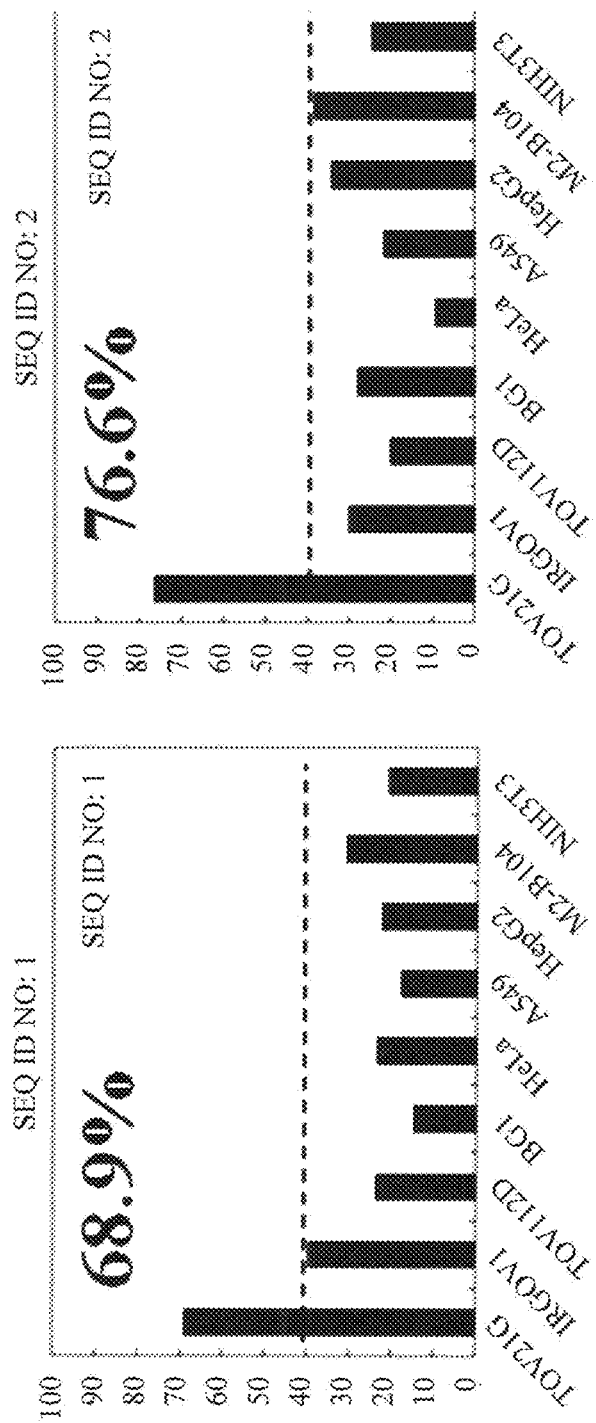
FIG. 4(A)-4(C), capture rates of the aptamer-conjugated magnetic beads to different histologically-classified ovarian cancer cells and other non-ovarian cancer cells, wherein (A) indicates the capture rates of the aptamer specific for clear-cell type ovarian cancer cell; (B) indicates the capture rates of the aptamer specific for endometrioid-cell type ovarian cancer cell; (C) indicates the capture rates of the aptamer specific for serous-cell type ovarian cancer cell.
Figure 4B:
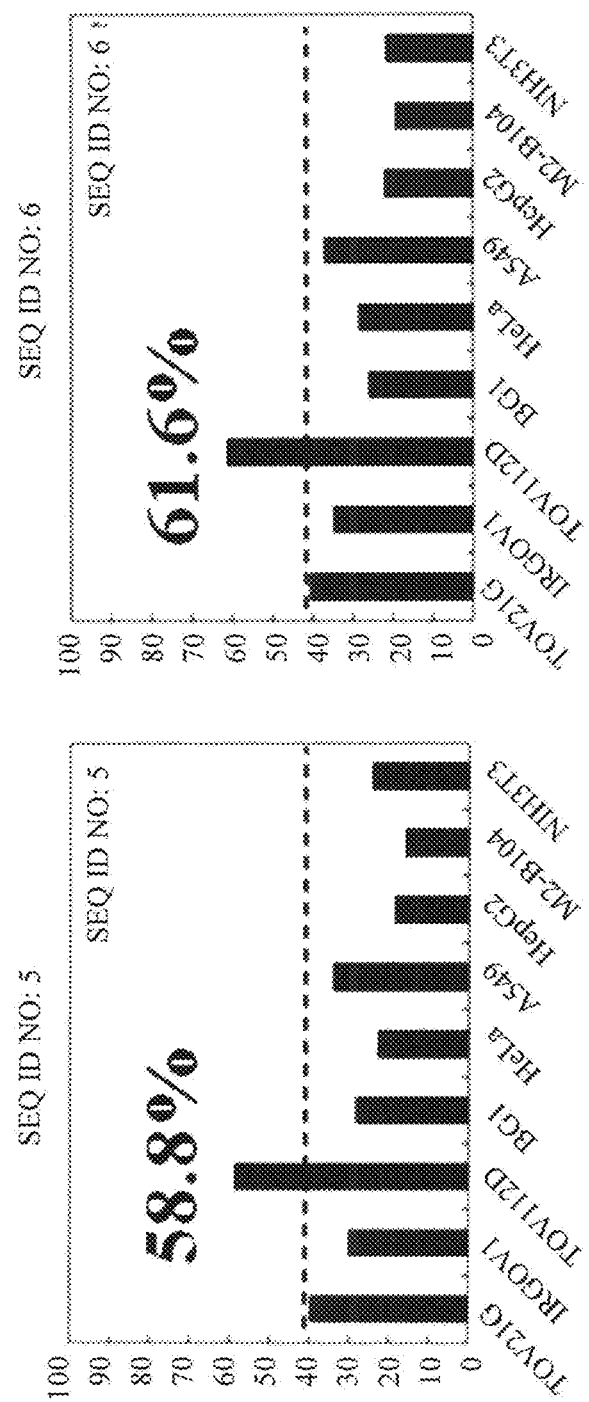
Figure 4C:
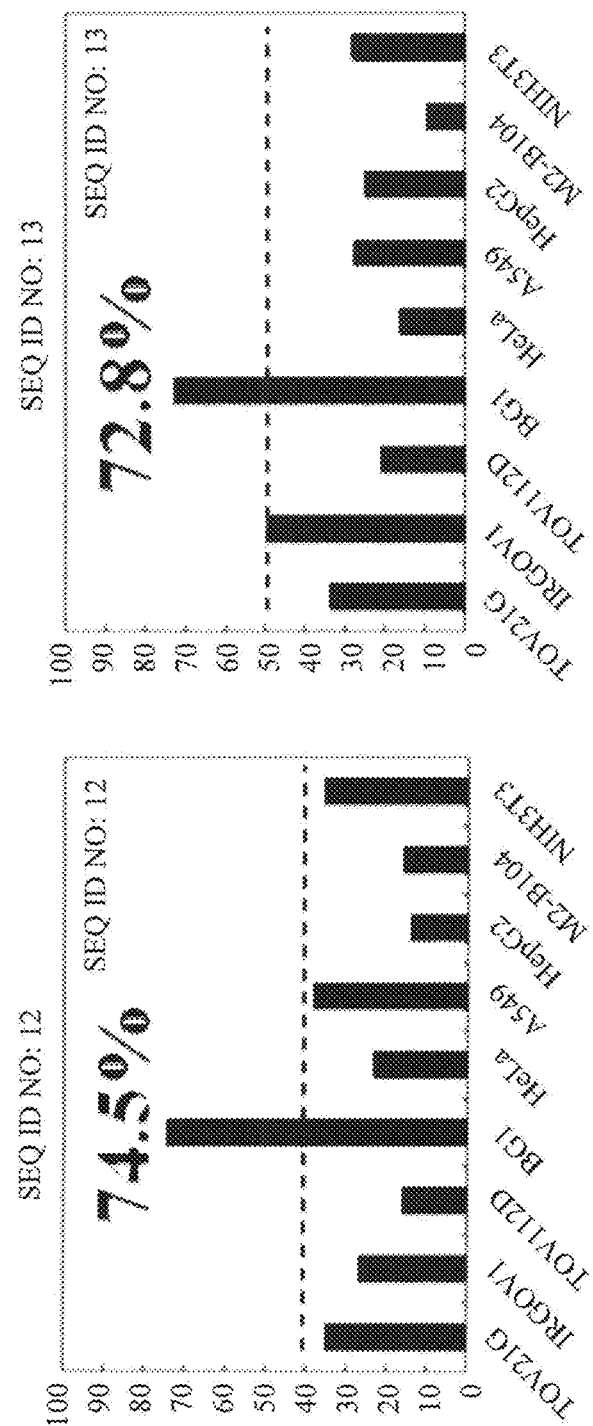

More specifically, as shown in FIG. 4(A), the capture rates of SEQ ID NO: 1, SEQ ID NO: 2, SEQ ID NO: 3, and SEQ ID NO: 4 towards TOV21G are 68.9%, 76.6%, 81.8%, and 79.8%, respectively; as shown in FIG. 4(B), the capture rates of SEQ ID NO: 5, SEQ ID NO: 6, and SEQ ID NO: 7 towards TOV112D are 58.8%, 61.6%, and 62.5%, respectively, whereas the capture rate of SEQ ID NO: 9 towards IGROV1 is 53.0%; as shown in FIG. 4(C), the capture rates of SEQ ID NO: 12 and SEQ ID NO: 13 towards BG1 are 74.5% and 72.8%, respectively. Besides, according to FIG. 4(B), the capture rates of SEQ ID NO: 10 towards TOV21G, BG1, and IGROV1 are 51.3%, 51.8%, and 52.1%, respectively. The aptamers of the present invention are thus proven to bind selectively to different histologically-classified ovarian cancer cells with high affinities ranging from 53.0-81.8%, but bind significantly less to other cancer cells with average affinity of 30%. As a result, the aptamers of the present invention are ovarian cancer-specific aptamers.

TABLE 3

| Aptamer | Cell line | | | | | | | | | |
|---|---|---|---|---|---|---|---|---|---|---|
| | TOV21G | TOV112D | BG1 | IGROV1 | HeLa | MCF7 | A549 | HepG2 | M2-B104 | NIH3T3 |
| Epithelial enriched beads | + | + | ++ | ++ | ++ | ++++ | +++ | + | + | + |
| SEQ ID NO: 1 | +++ | + | + | ++ | + | + | + | + | ++ | + |
| SEQ ID NO: 2 | ++++ | + | ++ | ++ | + | ++ | + | ++ | ++ | + |
| SEQ ID NO: 3 | ++++ | ++ | + | ++ | + | + | + | + | + | + |
| SEQ ID NO: 5 | ++ | +++ | ++ | ++ | + | ++ | ++ | + | + | + |
| SEQ ID NO: 6 | ++ | +++ | + | ++ | ++ | ++ | ++ | + | + | + |
| SEQ ID NO: 7 | ++ | +++ | ++ | ++ | + | + | ++ | + | + | + |
| SEQ ID NO: 8 | ++ | +++ | + | + | + | ++ | ++ | ++ | + | + |
| SEQ ID NO: 9 | ++ | + | + | +++ | + | ++ | + | + | + | + |
| SEQ ID NO: 10 | +++ | + | +++ | +++ | + | ++ | + | + | ++ | + |
| SEQ ID NO: 12 | ++ | + | +++ | ++ | + | ++ | ++ | + | + | ++ |
| SEQ ID NO: 13 | ++ | + | +++ | ++ | + | + | ++ | + | + | ++ |
| SEQ ID NO: 14 | +++ | + | + | ++ | + | + | + | + | ++ | + |
| SEQ ID NO: 15 | ++++ | + | ++ | ++ | + | ++ | + | ++ | ++ | + |
| SEQ ID NO: 16 | ++++ | ++ | + | ++ | + | + | + | + | + | + |
| SEQ ID NO: 17 | ++++ | + | + | ++ | + | + | + | + | ++ | ++ |
| SEQ ID NO: 18 | ++ | +++ | ++ | ++ | + | ++ | ++ | + | + | + |
| SEQ ID NO: 19 | ++ | +++ | ++ | ++ | ++ | ++ | ++ | + | + | + |
| SEQ ID NO: 20 | ++ | +++ | ++ | ++ | + | + | ++ | + | + | + |
| SEQ ID NO: 21 | ++ | +++ | + | + | + | ++ | ++ | ++ | + | + |
| SEQ ID NO: 22 | ++ | + | + | +++ | + | ++ | + | + | ++ | ++ |
| SEQ ID NO: 23 | +++ | + | +++ | +++ | + | ++ | + | + | ++ | + |
| SEQ ID NO: 24 | ++ | + | ++ | ++ | + | ++ | + | + | ++ | + |
| SEQ ID NO: 25 | ++ | + | +++ | ++ | + | ++ | ++ | + | + | ++ |
| SEQ ID NO: 26 | ++ | + | +++ | + | + | + | ++ | ++ | + | ++ |

The above results indicate that the aptamers of the present invention exhibit high specificity to different histologically-classified ovarian cancer cells but merely bind to other non-ovarian cancer cells with low binding affinity.

In conclusion, the aptamers of the present invention possess high specificity and high binding affinity to different histologically-classified ovarian cancer cells. Moreover, aptamers having small molecular weight are reusable and can be easily attached to other molecules. In comparison to antibodies, aptamers do not suffer from drawbacks of animal production; on the contrary, aptamers can be amplified with ease while maintaining accuracy of mass production. Thus, the aptamers of the present invention can readily replace the traditional method of using antibodies for the detection of ovarian cancer cells as well as distinguish ovarian cancer cells according to their histological classifications.

The ovarian caner-specific aptamer, method for detecting the existence of ovarian cancer cell in a subject, and microfluidic chip for executing the same according to the present invention are applicable and valuable to the industry. Those embodiments above are better results, and should not, however, be considered to limit the scope of the invention, it is contemplated that modifications will readily occur to those skilled in the art, which modifications will be within the spirit of the invention and scope of the appended claims.

What is claimed is:

1. A combination of ovarian cancer-specific aptamers, consisting of:
   a nucleic acid sequence specific for a clear-cell type ovarian cancer cell, a nucleic acid sequence specific for an endometrioid-cell type ovarian cancer cell, and a nucleic acid sequence specific for a serous-cell type ovarian cancer cell, wherein the nucleic acid sequence specific for the clear-cell type ovarian cancer cell is selected from
   the group consisting of SEQ ID NO: 14, SEQ ID NO: 15, SEQ ID NO: 16, SEQ ID NO: 17, SEQ ID NO: 23, and any combination thereof;
   the nucleic acid sequence specific for the endometrioid-cell type ovarian cancer cell is selected from the group consisting of SEQ ID NO: 18, SEQ ID NO: 19, SEQ ID NO: 20, SEQ ID NO: 21, SEQ ID NO: 22, SEQ ID NO: 23, SEQ ID NO: 24, and any combination thereof; and
   the nucleic acid sequence specific for the serous-cell type ovarian cancer cell is selected from the group consisting of SEQ ID NO: 23, SEQ ID NO: 25, SEQ ID NO: 26, and any combination thereof.

2. The combination of claim 1, wherein the aptamer contains at least one stem-loop secondary structure.

3. A method for detecting the existence of ovarian cancer cell in a subject, comprising:
   contacting a sample from the subject with the combination of ovarian cancer-specific aptamers of claim 1; and
   detecting the existence of the ovarian cancer cell in the sample bounded with the aptamer of step (a).

4. The method of claim 3, wherein the aptamer is conjugated to a label and the label is a fluorescence label, a luminescence label, a radioactive isotope, an enzymatic label, or a biotin.

5. The method of claim 3 further comprises conjugating the aptamer to a surface of a magnetic bead to form an aptamer-conjugated magnetic bead.

6. The method of claim 5, wherein the ovarian cancer cell is captured by the aptamer-conjugated magnetic bead and a magnetic field is used to isolate the aptamer-conjugated magnetic bead bound with the ovarian cancer cell.

7. A microfluidic chip, comprising the combination of ovarian cancer-specific aptamers of claim 1.

* * * * *